United States Patent
Zhang et al.

(10) Patent No.: US 8,496,586 B2
(45) Date of Patent: *Jul. 30, 2013

(54) BREAST ULTRASOUND EXAMINATION INCLUDING SCANNING THROUGH CHESTWARDLY COMPRESSING MEMBRANE AND PROCESSING AND DISPLAYING ACQUIRED ULTRASOUND IMAGE INFORMATION

(75) Inventors: Wei Zhang, Union City, CA (US); Jiayu Chen, Palo Alto, CA (US); Thomas P. Neff, Newark, CA (US); Michael E. Reed, Sunnyvale, CA (US); Jeanine M. Rader, Rockford, IL (US); Douglas G. Summers, Palo Alto, CA (US); Shih-Ping Wang, Los Altos, CA (US); Tor C. Anderson, Mountain View, CA (US); Zengpin Yu, Palo Alto, CA (US); Tommy Earl Cupples, Columbia, SC (US)

(73) Assignee: U Systems, Inc., Sunnyvale, CA (US)

( * ) Notice: Subject to any disclaimer, the term of this patent is extended or adjusted under 35 U.S.C. 154(b) by 534 days.

This patent is subject to a terminal disclaimer.

(21) Appl. No.: 12/760,382

(22) Filed: Apr. 14, 2010

(65) Prior Publication Data

US 2010/0280375 A1 Nov. 4, 2010

Related U.S. Application Data

(63) Continuation of application No. 11/439,093, filed on May 23, 2006, now Pat. No. 7,727,151, and a continuation-in-part of application No. 11/587,078, filed as application No. PCT/US2005/014321 on Apr. 26, 2005, now abandoned, application No. 12/760,382, which is a continuation-in-part of application No. 12/545,201, filed on Aug. 21, 2009, now Pat. No. 7,828,733, which is a continuation of application No. 10/997,293, filed on Nov. 23, 2004, now Pat. No. 7,615,008.

(60) Provisional application No. 60/684,622, filed on May 24, 2005, provisional application No. 60/565,698, filed on Apr. 26, 2004, provisional application No. 60/577,078, filed on Jun. 4, 2004, provisional application No. 60/629,007, filed on Nov. 17, 2004, provisional application No. 60/525,640, filed on Nov. 28, 2003, provisional application No. 60/577,326, filed on Jun. 4, 2004.

(51) Int. Cl.
*A61B 8/00* (2006.01)

(52) U.S. Cl.
USPC .......................... 600/437; 600/407; 600/443

(58) Field of Classification Search
USPC ................................................. 600/437, 443
See application file for complete search history.

(56) References Cited

U.S. PATENT DOCUMENTS

| 6,317,617 B1 | 11/2001 | Gilhuijs |
| 2003/0007598 A1 | 1/2003 | Wang et al. |

(Continued)

FOREIGN PATENT DOCUMENTS

WO WO03/010130 A1 12/2003

OTHER PUBLICATIONS

Richter et al. Detection of malignant and benign breast lesions with an automated US system results in 120 cases, Radiology, vol. 205 p. 823-830, 1997.

*Primary Examiner* — Unsu Jung
*Assistant Examiner* — Saurel J Selkin
(74) *Attorney, Agent, or Firm* — Cooper & Dunham LLP

(57) ABSTRACT

Navigation among breast ultrasound volumes derived from different volumetric ultrasonic scans of a same breast is described. On a display of a breast ultrasound workstation, a first image derived from a first ultrasonic volume is displayed. A user election of a source region of interest (ROI) in the first image is received. A destination ROI within a second ultrasonic volume is identified that at least roughly corresponds to a same locality of tissue in the breast as the source ROI. A second image derived from the second ultrasonic volume and including the destination ROI is displayed, the destination ROI being highlighted.

16 Claims, 40 Drawing Sheets

U.S. PATENT DOCUMENTS

2003/0212327 A1 11/2003 Wang et al.
2005/0113651 A1 5/2005 Wood et al.
2005/0171430 A1 8/2005 Zhang et al.
2006/0004278 A1 1/2006 Giger et al.

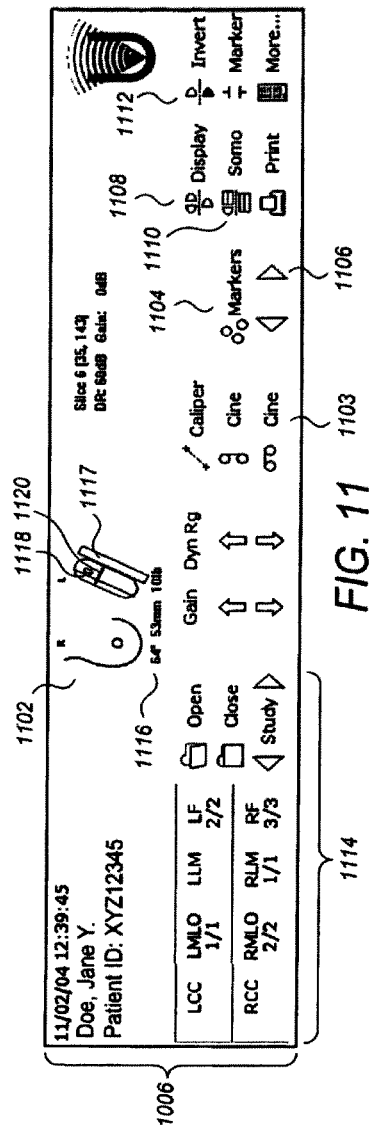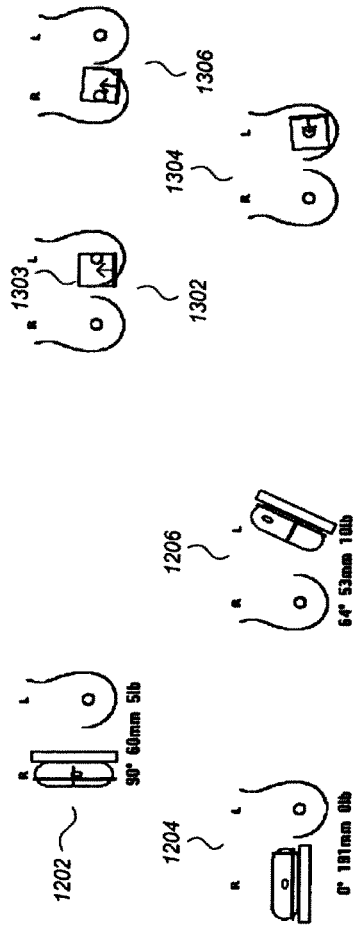
FIG. 11
FIG. 12
FIG. 13

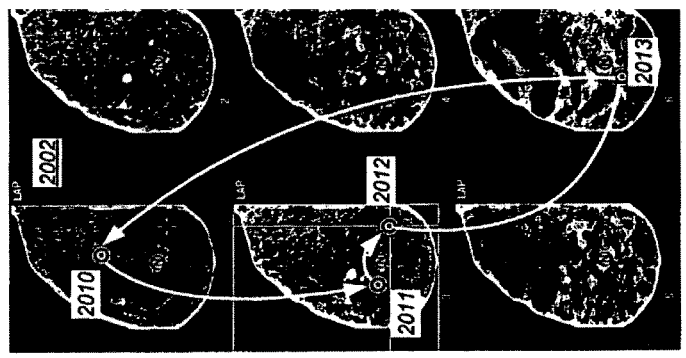
FIG. 20
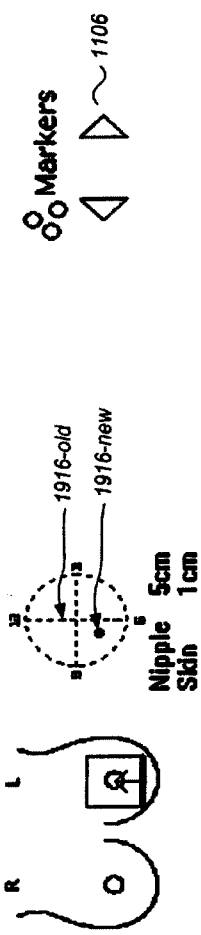
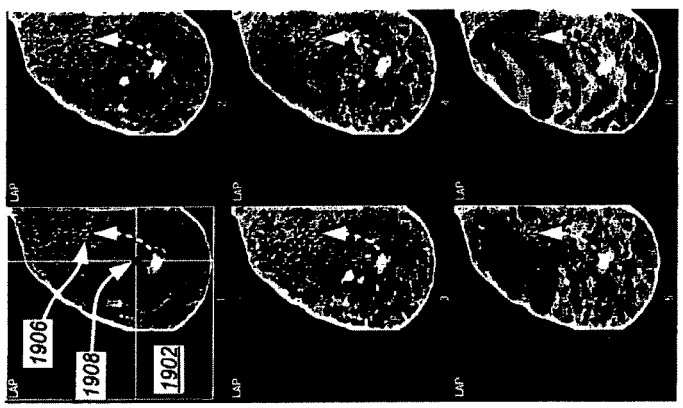
FIG. 19

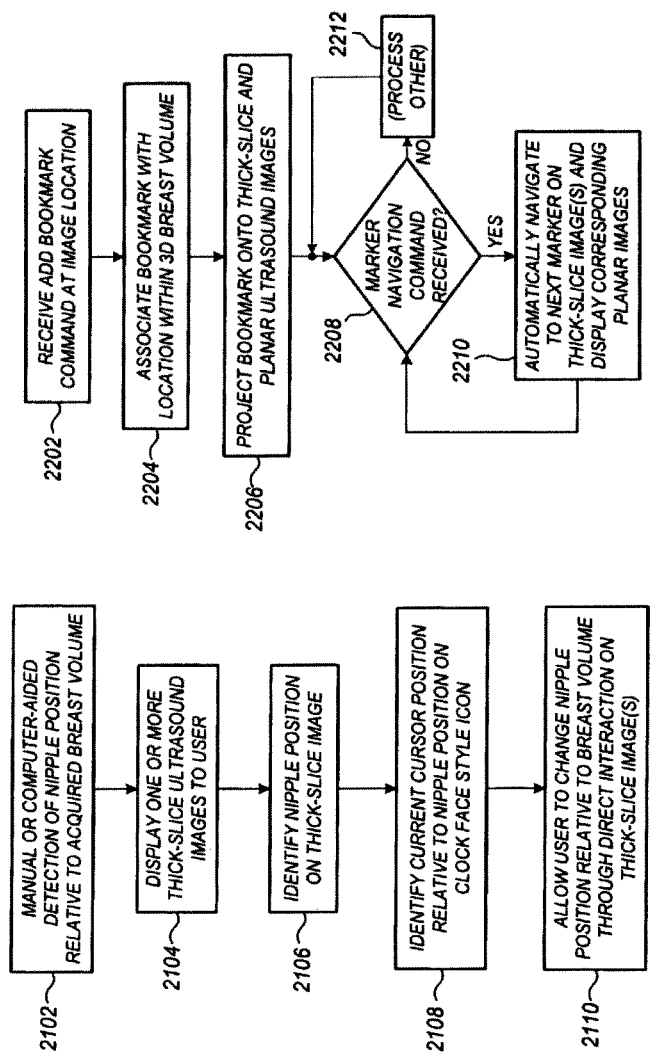

BREAST ULTRASOUND EXAMINATION INCLUDING SCANNING THROUGH CHESTWARDLY COMPRESSING MEMBRANE AND PROCESSING AND DISPLAYING ACQUIRED ULTRASOUND IMAGE INFORMATION

CROSS-REFERENCE TO RELATED APPLICATIONS

This application is a continuation of Ser. No. 11/439,093 filed May 23, 2006 and now U.S. Pat. No. 7,727,151, which claims the benefit of U.S. Provisional Application No. 60/684,622, filed May 24, 2005, each of which is incorporated by reference herein. This application is also a continuation-in-part of Ser. No. 11/587,078 filed Jun. 18, 2008 and now abandoned, which is a U.S. national stage filing of International Application No. PCT/US05/14321 filed Apr. 26, 2005, which claims priority to each of the following U.S. Provisional Applications: Ser. No. 60/565,698 filed Apr. 26, 2004, Ser. No. 60/577,078 filed Jun. 4, 2004, and Ser. No. 60/629,007 filed Nov. 17, 2004. This application is also a continuation-in-part of Ser. No. 12/545,201 filed Aug. 21, 2009 and now U.S. Pat. No. 7,828,733, which is a continuation of Ser. No. 10/997,293 filed Nov. 23, 2004, now U.S. Pat. No. 7,615,008, which claims the benefit of each of the following U.S. Provisional Applications: Ser. No. 60/525,640 filed Nov. 28, 2003, and Ser. No. 60/577,326 filed Jun. 4, 2004.

FIELD

This patent specification relates to medical ultrasound imaging. More particularly, this patent specification relates to processing and/or display of breast ultrasound information for breast cancer screening and/or diagnosis purposes and a versatile breast ultrasound scanning apparatus and related methods.

BACKGROUND

The subject matter of this patent specification relates to the processing and display of breast ultrasound information as described, for example, in the commonly assigned US 2003/0007598A1 and US 2003/0212327A1, each of which is incorporated by reference herein. The subject matter of this patent specification also relates to the processing and display of breast ultrasound information acquired according to the commonly assigned U.S. Prov. Ser. No. 60/629,007 filed Nov. 17, 2004, and U.S. Ser. No. 10/997.283 filed Nov. 23, 2005, each of which is incorporated by reference herein.

In one or more of the above-referenced disclosures, there are presented convenient schemes for viewer navigation between (a) thick-slice images generated from a breast volume and (b) planar ("single-slice") images for that breast volume, as well as navigation in the other direction from the planar images to the thick-slice images. Thus, for example, a viewer can click on a region of interest (ROI) in one of the thick-slice images, and the display will automatically show the appropriate corresponding planar images that pass through that ROI in the breast volume, and will also place markers thereon corresponding to that ROI. This is a valuable capability because the viewer is provided with multiple image presentations of the ROI without having to scan through the various images for corresponding ROIs, which can be a time-consuming and stamina-reducing task. Rather, the viewer simply clicks on the ROI on the image being examined, and that location is automatically "navigated to" and highlighted by the workstation display system in the other views. Generally speaking, such automated navigation between views is not problematic when there is a single ultrasound volume for each breast, because the absolute location of the ROI within the breast becomes known as soon as the viewer clicks on the selected point.

It has been found desirable in many instances to obtain multiple volumetric ultrasound scans of the same breast during the same session. With reference to FIGS. 28-32 infra, the multiple volumetric ultrasound scans can be head-on scans taken at differing positions or orientations, each of the scans being taken while a taut surface compresses the breast in a generally chestward direction and an ultrasound probe is swept thereacross. In other cases, there may be scans taken while the breast is compressed along differing mammographic planes such as the CC or MLO planes, as iconically represented, for example, by the body marker icons 1202, 1204, and 1206 of FIG. 12 infra.

The use of multiple volumetric scans can overcome certain disadvantages associated with of single-volumetric scan scenarios. In particular, for any particular volumetric ultrasound scan, there can be shadowing or other obfuscations of interesting tissue structures because of the presence of other tissue structures that are "in the way" during the scanning process. When there is only a single volumetric scan available, there is generally no way for the viewer to know what structures are behind or underneath the obfuscating structures. However, when there are multiple volumetric ultrasound scans available that were taken from different positions/directions, the viewer can consult a second ultrasound volume to better see the obfuscated structure.

It would be desirable to streamline the process of viewing additional ultrasonic volumes by providing for automated navigation between a first ultrasonic volume of a breast acquired during a first volumetric scan thereof and a second ultrasonic volume of the same breast taken during a second volumetric scan thereof, the first and second volumetric scans having been taken at differing positions and/or orientations.

Volumetric ultrasound scanning of the breast has been proposed as a complementary modality for breast cancer screening as described, for example, in the commonly assigned US 2003/007598A1 published Jan. 9, 2003, which is incorporated by reference herein. Whereas a conventional two-dimensional x-ray mammogram only detects a summation of the x-ray opacity of individual slices of breast tissue over the entire breast, ultrasound can separately detect the sonographic properties of individual slices of breast tissue, and therefore may allow detection of breast lesions where x-ray mammography alone fails. Another well-known shortcoming of x-ray mammography practice is found in the case of dense-breasted women, including patients with high content of fibroglandular tissues in their breasts. Because fibroglandular tissues have higher x-ray absorption than the surrounding fatty tissues, portions of breasts with high fibroglandular tissue content are not well penetrated by x-rays and thus the resulting mammograms contain reduced information in areas where fibroglandular tissues reside.

The commonly assigned WO 2004/030523A2 published on Apr. 15, 2004, which is incorporated by reference herein, describes a full-field breast ultrasound (FFBU) scanning apparatus that compresses a breast along a standard mammographic view plane such as the craniocaudal (CC) plane, the mediolateral oblique (MLO) plane, etc., and ultrasonically scans the breast. A scanning surface comprises an at least partially conformable, substantially taut membrane or film sheet compressing one side of the breast. The other side of the breast is compressed by a compression plate, optionally with the aid of an inflatable air bladder. A transducer translation mechanism holds a transducer surface against an opposite side of the film sheet while translating the transducer thereacross to scan the breast. An irrigation system automatically maintains a continuous supply of coupling agent at an interface between the transducer surface and the film sheet as the transducer is translated.

The operation of the scanning apparatus described in WO 20041030523A2, supra, depends at least in part on the "pendulous" properties of the breast, that is, the ability of the breast to extend away from the chest wall onto the scanning surface for compression along the axial plane (for CC scan), coronal plane (for lateral scan), or other anti-coronal plane lying between the axial and coronal planes (e.g., for MLO scan). As used herein, the term anti-coronal plane refers to a plane that lies generally perpendicular to the coronal plane. As with conventional x-ray mammography, the presumption is made that most breasts will have such pendulous properties. While effective for a large portion of the population, problems arise for patients having smaller breasts without pendulous properties, because much of the diagnostically relevant breast tissue cannot extend outward over the scanning surface by a sufficient amount. Moreover, even for patients with pendulous breasts, there can be difficulty in imaging the tissue near the chest wall that does not extend onto the scanning surface.

One important quality a breast ultrasound scanning apparatus is ease of mechanical control and manipulation. Generally speaking, acquiring volumetric ultrasonic breast scans can be a highly patient-specific process, not only in view of the wide variety of breast sizes, shapes, and densities, but also in view of the wide variety of different patient body shapes near and around the breast area (e.g., shoulder contours, sternum contours, ribs contours, etc.) A scanning apparatus that is versatile and easily adaptable to the particular patient being scanned can therefore facilitate optimal acquisition of ultrasonic views of the breast volume. Moreover, ease of use can also positively affect the salability and commercial success of the scanning apparatus.

Accordingly, it would be desirable to provide a breast ultrasound scanning apparatus that is easy to mechanically control and manipulate for facilitating high-quality volumetric ultrasonic scans across a variety of different patients.

It would be further desirable to provide a breast ultrasound scanning system that is capable of accommodating small, non-pendulous breasts as well as pendulous breasts.

It would be further desirable to provide a breast ultrasound scanning apparatus that can achieve high-quality ultrasound imaging even near the chest wall of the patient.

It would be further desirable to provide such a breast ultrasound scanning apparatus that is comfortable for the patient, has a cost-efficient patient throughput rate, and that is cost-efficient to own even for smaller medical clinics.

SUMMARY

A method, system, and associated computer program product is provided for automated navigation between a first ultrasonic volume of a breast acquired during a first volumetric scan thereof and a second ultrasonic volume of the same breast taken during a second volumetric scan thereof. On a display of a breast ultrasound workstation, a first image is displayed, the first image being derived from the first ultrasonic volume and comprising one of (i) a thick-slice image representing the first ultrasonic volume within a slab-like subvolume thereof, and (ii) a planar image representing the first ultrasonic volume along a plane therethrough. A user selection of a source region of interest (ROI) in the first image is received. The source ROI is mapped from the first image into the first ultrasonic volume according to the known position of the slab-like subvolume or plane within the first ultrasonic volume. The source ROI is then mapped from within the first ultrasonic volume into a corresponding destination ROI within the second ultrasonic volume of the breast. The destination ROI is then mapped onto a second image, the second image comprising one of (i) a thick-slice image representing the second ultrasonic volume within a slab-like subvolume thereof, and (ii) a planar image representing the second ultrasonic volume along a plane therethrough, this mapping being in accordance with a known position of the slab-like subvolume or plane within the second ultrasonic volume. The second image is displayed to the viewer with the position of the destination ROI therein being highlighted.

In one preferred embodiment, the mapping from the source ROI within the first ultrasonic volume into the corresponding destination ROI within the second ultrasonic volume first comprises identifying a nipple location of the breast in each of the first and second ultrasonic volumes thereof. A projected location of the source ROI onto a first coronal reference plane passing through the nipple location within the first ultrasonic volume is then identified. A Cartesian offset between the projected source ROI location and the nipple location on the first coronal reference plane is then determined. That Cartesian offset is then transferred to a second coronal reference plane to identify a transferred offset point thereon, the second coronal reference plane passing through the nipple location within the second ultrasonic volume. The transferred offset point is then backprojected from the second coronal reference plane into the second ultrasonic volume.

In another preferred embodiment, accommodations are made for compression of the breast along an anti-coronal plane (i.e., along a plane perpendicular to the coronal plane, which would include CC, MLO, and LAT, for example) during one or both of the volumetric scans. In particular, where the breast was so compressed during the first scan or the second scan (but not both), the transferred point on the second coronal reference plane is modified according to an elastic mapping between a coronal projection of the anti-coronally-compressed breast onto a coronal projection of the non-anti-coronally-compressed breast. If the breast was so compressed for both volumetric scans, the breast being compressed along a first anti-coronal plane during the first volumetric scan thereof and compressed along a second anti-coronal plane during the second volumetric scan thereof, the transferred point on the second coronal reference plane is modified according to an elastic mapping between a coronal projection of the breast as compressed along the first anti-coronal plane and a coronal projection of the breast as compressed along the second anti-coronal plane. The elastic mapping is determined at least in part according to a measured compression force and a distance between compression plates during breast compression along the anti-coronal plane.

An apparatus and related methods for full-field breast ultrasound (FFBU) scanning of a breast of a patient are provided, the apparatus at least partially compressing the breast in a generally chestward direction and acquiring scans thereof. The apparatus is particularly useful for patients in fully supine positions or partially supine (i.e., reclining) positions, although it may be used on upright patients as well. The apparatus comprises a compression/scanning assembly having an at least partially self-contained, pod-like character that is adapted for easy manipulation by a user. The compression/scanning assembly comprises an ultrasound transducer and an at least partially conformable membrane in a substantially taut state, the membrane having a first surface for contacting the breast and a second surface opposite the first surface, the transducer being swept across the second surface in contact therewith to scan the breast.

In one preferred embodiment, the compression/scanning assembly is maintained at an end of a movable support arm that is, in turn, coupled to a frame. The end of the support arm has all three translational degrees of freedom (e.g., x, y, and z) relative to the frame, and the compression/scanning assembly has all three rotational degrees of freedom (e.g., pitch, roll, and yaw) relative to the end of the movable support arm. Preferably, the support arm supports the compression/scanning assembly in a springable, partially frictionable manner to be either (i) neutrally buoyant in space, or (ii) to have a light net downward weight (e.g., 2-3 pounds) for breast compression, while allowing for easy user manipulation. In addition to being easy to manipulate, the scanning apparatus further promotes patient comfort and reliable scanning because the patient can comfortably breathe during the procedure without confounding the scanning results, because the compression/scanning assembly rises up and down (or in and out) with the patient's chest. Optionally, the support arm may comprise potentiometers to allow position and orientation sensing for the compression/scanning assembly, or other types of position and orientation sensing (e.g., gyroscopic, magnetic, optical) can be used. Further position and orientation sensors can optionally be placed on the patient's chest to detect relative motion between the compression/scanning assembly and the patient, where desired.

In one preferred embodiment, the compression/scanning assembly comprises a housing within which the transducer is disposed, the housing including an aperture across which the membrane is positioned. Preferably, both the membrane and the housing are transparent at locations that allow the user to view the breast surface through the compression/scanning assembly during the positioning and scanning process. In one preferred embodiment, a lateral support element is provided extending from the membrane toward the breast for gentle lateral confinement of the breast during the scans, the lateral support element comprising an at least partially pliable material such as a rubber material.

In another preferred embodiment, the compression/scanning assembly is mechanically separated from the support arm, being fully supported and manipulated by the user's hands. Optionally, the compression/scanning assembly may be electrically coupled to an ultrasound processor through a cable extending from the support arm, the cable also providing backup support by suspending the compression/scanning assembly above the floor in case it is accidentally released by the user. In still other preferred embodiments, the compression/scanning assembly uses wireless digital communications or other electromagnetic radiation-based communications to transfer signals to the ultrasound processor.

BRIEF DESCRIPTION OF THE DRAWINGS

FIG. 11 illustrates a menu bar of a breast ultrasound display according to a preferred embodiment;

FIGS. 12 and 13 illustrate body marker icons according to a preferred embodiment;

FIG. 19 illustrates an array of thick-slice images with viewer-shifted nipple markers, a body marker icon, and a frontal breast icon according to a preferred embodiment;

FIG. 20 illustrates an array of thick-slice images with nipple markers and bookmarks, a marker display button, and marker navigation buttons according to a preferred embodiment;

FIGS. 21 and 22 illustrate breast ultrasound volume acquisition, processing, and display according to one or more preferred embodiments;

DESCRIPTION

Figure 1:
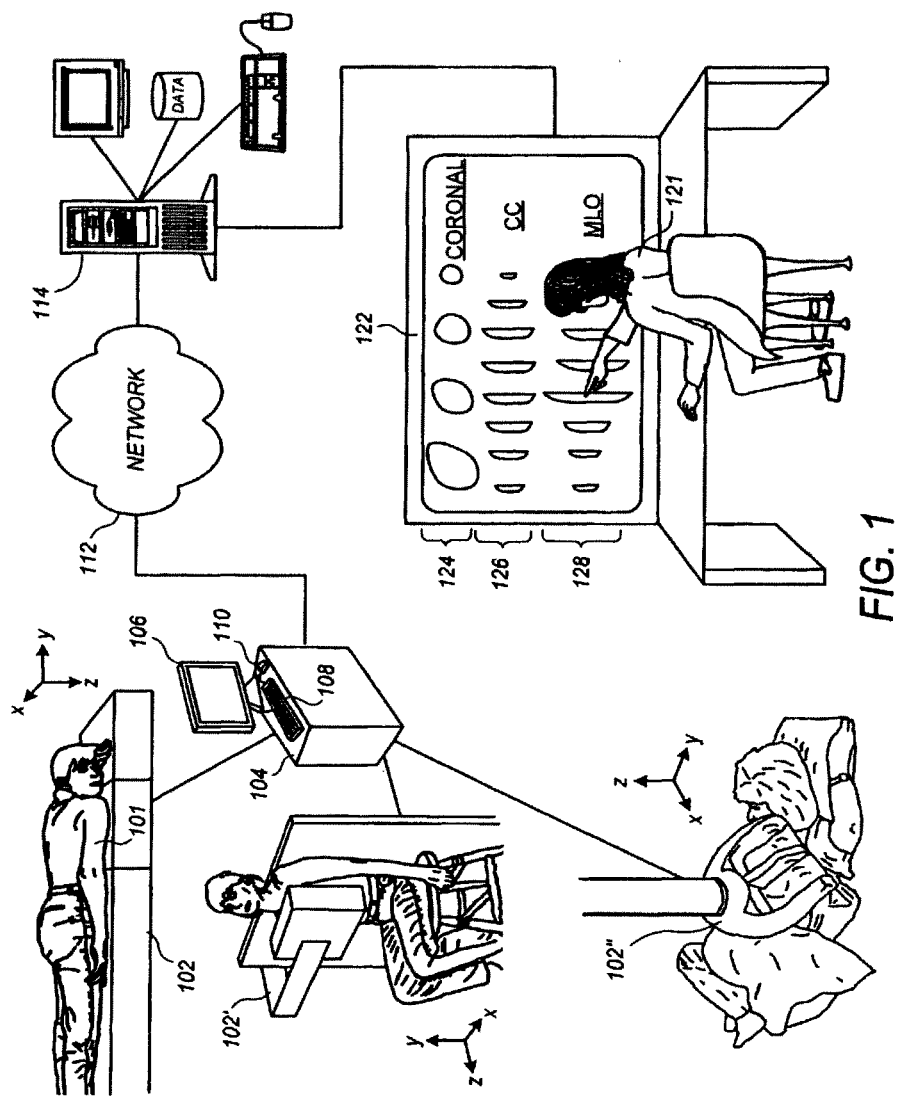
FIG. 1 illustrates a conceptual diagram of a breast cancer screening and/or diagnosis system according to a preferred embodiment.

FIG. 1 illustrates a conceptual diagram of a breast cancer screening and/or diagnosis system according to a preferred embodiment. The breast of a patient 101 is ultrasonically scanned by an automated scanning apparatus while the patient is in a prone position (device 102), an upright position (device 102'), a supine position (device 102") or other position (not shown). By reducing the required ultrasonic penetration depth to the chest wall, scanning of a chestwardly compressed breast can occur at higher frequencies, e.g., 10-20 MHz, which can yield very high resolution images sufficient to facilitate detection of microcalcifications or other structures on the order of 1 mm near the chest wall. However, it is to be appreciated that the scope of the preferred embodiments is not limited to a chestwardly-compressed scenario, with breast ultrasound information processing and display according to the preferred embodiments being generally useful with any scanning system from which a three-dimensional volumetric representation of a sonographic property of the breast can be derived.

Breast scans are obtained under the control of a scanning engine and workstation 104 including, for example, a monitor 106, keyboard 108, a mouse 110, and a scanning engine (not shown). During or after the scanning process, the ultrasound scan data is provided across a computer network 112 to an ultrasound server 114 that processes and generates display information according to the functionalities described herein.

The ultrasound server 114 may perform other HIS/RIS (hospital information system/radiology information system) activities such as archiving, scheduling, etc. It is to be appreciated that the processing of the ultrasound scan data may be performed by any of a variety of different computing devices coupled to the computer network 112 in various combinations without departing from the scope of the preferred embodiments.

According to a preferred embodiment, a viewing workstation 122 is provided that displays an array 124 of coronal thick-slice images to a clinician 121, each coronal thick-slice image representing a sonographic property of the breast within a slab-like subvolume thereof substantially parallel to a coronal plane. As used herein, the term "clinician" generically refers to a medical professional, such as a radiologist, or other person that analyzes medical images and makes clinical determinations therefrom, it being understood that such person might be titled differently, or might have varying qualifications, depending on the country or locality of their particular medical environment. In another preferred embodiment, as shown in FIG. 1, one or more standard-plane thick slice image arrays are displayed to the clinician 121, such as a craniocaudal (CC) thick-slice image array 126 and a mediolateral oblique (MLO) thick-slice image array 128.

In another preferred embodiment (not shown), the clinician is also provided with the ability to view individual planar ultrasound slices (along sagittal, axial, coronal, or other cutplanes through the three-dimensional breast volume) as desired. An example of one desirable planar ultrasound display and navigation scheme is provided in the commonly assigned US2003/0212327A1, supra, and in other preferred embodiments described herein.

Figure 2:
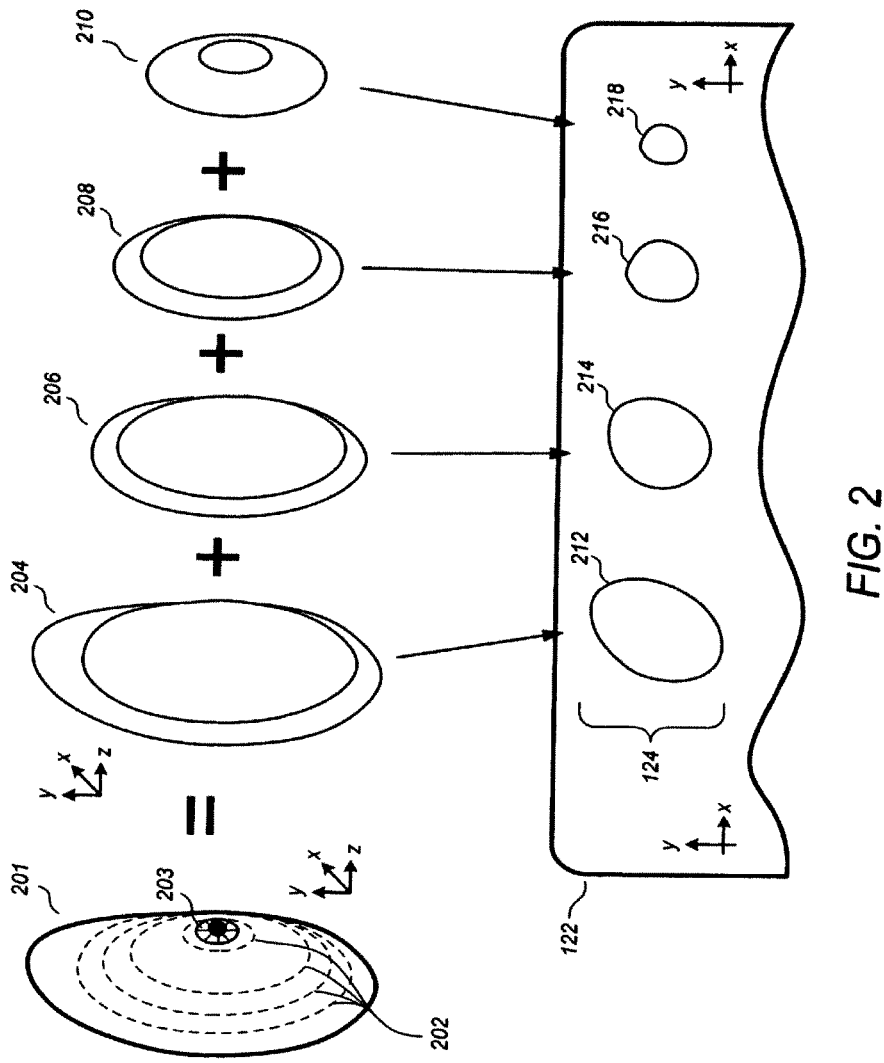
FIG. 2 illustrates a perspective view of a breast volume and slab-like subvolumes thereof substantially parallel to a coronal plane, and an array of two-dimensional coronal thick-slice images corresponding thereto.

FIG. 2 illustrates a perspective view of a breast volume 210 and coronal slab-like subvolumes 204-210 thereof substantially parallel to a coronal plane, along with the array 124 of two-dimensional coronal thick-slice images generated therefrom according to a preferred embodiment. The coronal slab-like subvolumes 204-210, which are separated by planes 202, correspond to the coronal thick-slice images 212-218, respectively. Generally speaking, the coronal slab-like subvolumes nearer to the chest wall (e.g., 204-206) have a larger cross-section in the coronal plane than the slab-like subvolumes nearer to the nipple 203 (e.g., 208-210). As used herein, coronal slab-like subvolumes refer generally to slab-like subvolumes within the breast that are roughly parallel to the chest wall of the patient. The coronal slab-like subvolumes 204-210 typically have a thickness in the range of 2-20 mm. Optionally, the coronal slab-like subvolumes can be gently contoured to more closely follow the contours of the chest wall. In such cases, the coronal slab-like subvolumes would have surfaces roughly reminiscent of a section of a hyperboloid, or roughly reminiscent of a potato chip.

Generally speaking, a coronal thick-slice image comprises an integration of a plurality of individual ultrasound slices lying within a coronal slab-like subvolume. Thus, for example, where the coronal slab-like subvolume 204 is represented by a three-dimensional voxel array V(x,y,z) of scalar values, the corresponding coronal thick-slice image 212 would be a two-dimensional pixel array $P_{COR}(x,y)$ of scalar values. In one preferred embodiment, each pixel value $P_{COR}(x,y)$ is simply computed as an arithmetic average along the corresponding voxel column at (x,y) having the voxel values $V(x,y,z_0), V(x,y,z_1), V(x,y,z_2), \ldots, V(x,y,z_N)$, where N is the number of individual ultrasound slices lying in the coronal slab-like subvolume. For clarity of description, the voxel column at (x,y) having the voxel values $V(x,y,z_0), V(x,y,z_1), V(x,y,z_2), \ldots, V(x,y,z_N)$ is expressed herein as $V_{xy}(z)$.

Techniques for integrating the component ultrasound slices into the coronal thick-slice images $P_{COR}(x,y)$ according to the preferred embodiments include arithmetic averaging, geometric averaging, reciprocal averaging, exponential averaging, and other averaging methods, in each case including both weighted and unweighted averaging techniques. Other suitable integration methods may be based on statistical properties of the population of component ultrasound slices at common locations, such as maximum value, minimum value, mean, variance, or other statistical algorithms.

Preferably, the coronal slab-like subvolumes have a thickness related to the size of the lesions to be detected. At an upper end, a larger thickness of 20 mm, for example, may be used if it is desirable to overlook most of the breast details and direct the user's attention to larger features on the order 10 mm in size. At a lower end, a smaller thickness of 2 mm, for example, may be used if it is desirable to view small structures, such as microcalcifications, on the order of 1 mm in size. Thicknesses in the range of 4 mm-10 mm are likely to be suitable for most breast cancer screening purposes.

In other preferred embodiments, the pixel value $P_{COR}(x,y)$ may be computed according to an algorithm that processes a neighborhood of voxel columns around the voxel column $V_{xy}(z)$, the algorithm being designed to result in coronal thick-slice images that emphasize lesions of a predetermined size range. In one such preferred embodiment, the integration method comprises weighting the voxels of the corresponding voxel column by a weighting vector and then summing the results, the weighting vector being computed according to neighborhood characteristics around that voxel column. This can be summarized by Eq. (1) below:

$$P_{COR}(x, y) = FUNC\{V_{xy}(z)\} = \sum_{n=1}^{N} W_{xy}(n)V_{xy}(z_n) \quad \{1\}$$

Using known three-dimensional segmentation and computer-aided detection (CAD) techniques, the locations and sizes of lesions in the coronal thick-slice volume are identified, either directly or by way of a mapping from the overall three-dimensional breast volume. Any of a variety of known three-dimensional segmentation and/or CAD algorithms can be used such as those discussed in U.S. Pat. No. 6,317,617 to Gilhuijs, Giger, and Bick, which is incorporated by reference herein. In one preferred embodiment, for a given voxel column, the weighting vector $W_{xy}(n)$ comprises peaks at locations lying within the lesions and valleys elsewhere, thus causing the resulting coronal thick-slice image to emphasize mass lesions in the output. In another preferred embodiment, the weighting vector $W_{xy}(n)$ can be computed as described in the commonly assigned WO 02/101303A1, which is incorporated by reference herein. The CAD-detected abnormalities can include microcalcifications, suspicious masses, and/or other known breast abnormalities.

Figure 3:
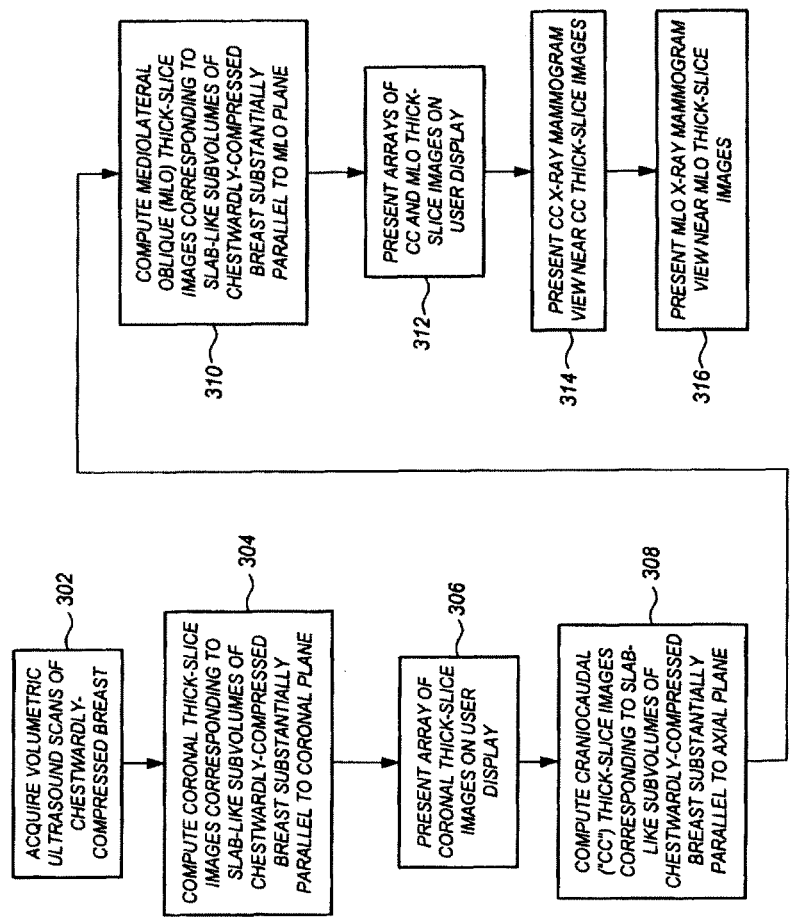
FIG. 3 illustrates a method for processing and displaying breast ultrasound information according to a preferred embodiment.

FIG. 3 illustrates a method for processing and displaying breast ultrasound information according to a preferred embodiment. At step 302, volumetric ultrasound scans of the chestwardly-compressed breast are acquired, either in real-time as the breast is being scanned, or in an off-line manner as from a database or archive of previously-acquired images. At step, 304, coronal thick-slice images are computed corresponding to slab-like subvolumes of the chestwardly-compressed breast substantially parallel to coronal plane. At step 306, the array of coronal thick-slice images is displayed on a user display, preferably in a side-by-side manner. However, a variety of different spatial arrangements of the coronal thick-slice images are within the scope of the preferred embodiments. For example, the array may be presented in circular or matrix fashion. In one preferred embodiment, all of the coronal thick-slice images collectively corresponding to the entire breast volume are simultaneously displayed to the viewer, so that the whole breast is effectively shown at the same time, thereby facilitating clinical workflow efficiency. In another preferred embodiment, the coronal thick-slice images can be progressively displayed at successive time intervals, either automatically or responsive to user controls.

According to one preferred embodiment, at step 308 craniocaudal (CC) thick-slice images, which are one type of standard-plane thick-slice image, are computed corresponding to slab-like subvolumes of the chestwardly-compressed breast substantially parallel to an axial plane, which corresponds to the CC view. At step 310 mediolateral oblique (MLO) thick-slice images, which are another type of standard-plane thick-slice image, are computed corresponding to slab-like subvolumes of the chestwardly-compressed breast substantially parallel to an MLO plane. At step 312, the arrays of CC and MLO thick-slice images are presented on the user display.

Figure 4:
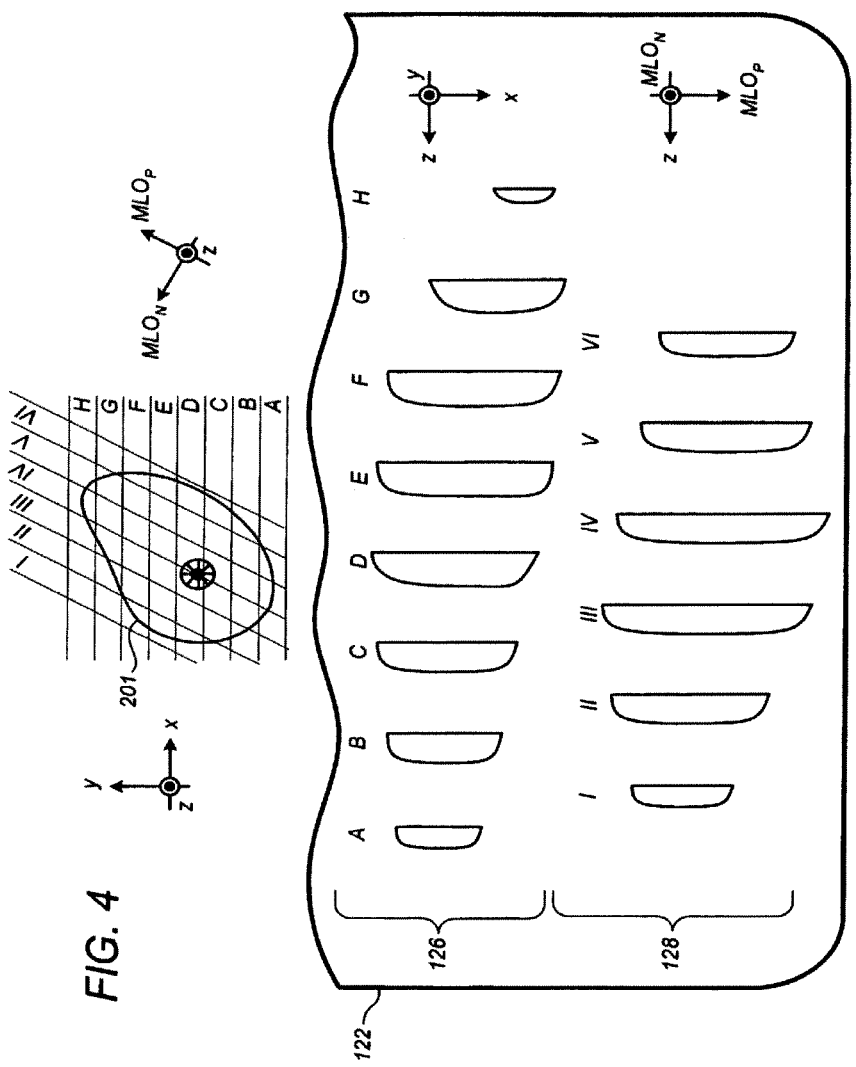
FIG. 4 illustrates a front view of a breast, a front view of slab-like subvolumes thereof substantially parallel to standard x-ray mammogram planes, and arrays of standard-plane thick-slice images corresponding thereto for display in conjunction with the coronal thick-slice images of FIG. 2 according to a preferred embodiment.

FIG. 4 illustrates a conceptual front view of the breast 210 upon which are drawn (i) front-view outlines of slab-like subvolumes A-H corresponding to CC slab-like subvolumes, and (ii) front-view outlines of slab-like subvolumes I-VI corresponding to MLO slab-like subvolumes. Also shown in FIG. 4 is a portion of the viewing workstation 122 illustrating the CC thick-slice image array 126 and the MLO thick-slice image array 128 with indicators mapping them into the slab-like subvolumes A-H and U-VI, respectively. The CC and MLO thick-slice image arrays can be generated from the three-dimensional breast volume in a manner analogous to that described in WO 02/101303A1, supra. As known in the art, the MLO plane is usually about 55 degrees away from the CC plane. It is to be appreciated, however, that a variety of angles for the MLO plane can be used without departing from the scope of the preferred embodiments, including 90 degrees (in which case it corresponds to the mediolateral "ML" view) or greater.

Figure 5:
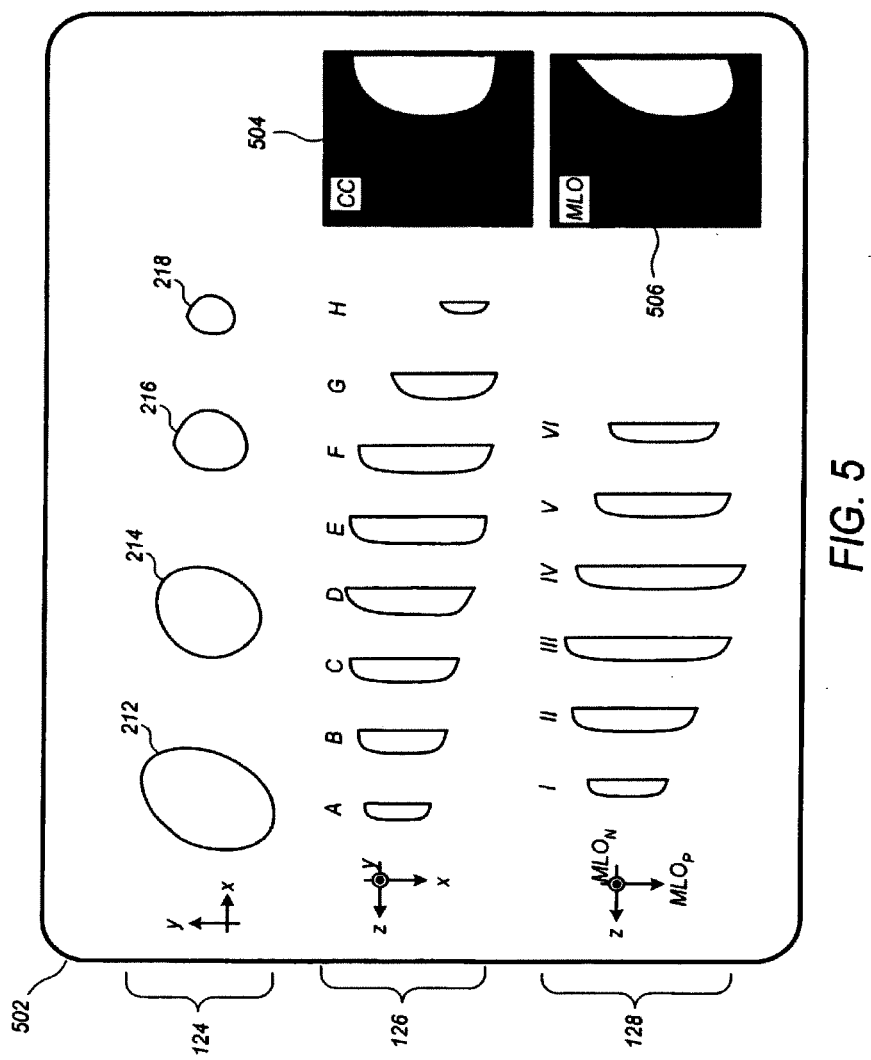
FIG. 5 illustrates a user display according to a preferred embodiment.

Referring again to FIG. 3, according to one preferred embodiment, standard CC and MLO x-ray mammogram views of the breast are displayed at steps 314 and 316, respectively. FIG. 5 illustrates a viewing workstation 502 similar to the viewing workstation 122, supra, with the addition of CC and MLO x-ray mammogram images 504 and 506, respectively, which can further facilitate screening and diagnosis through back-and-forth viewing of interesting areas. The CC and MLO x-ray mammogram images 504 and 506 are preferably in digitized form for practical reasons, although it is within the scope of the preferred embodiments for these to be film-based x-ray mammograms on a light-box background.

Figure 6A:
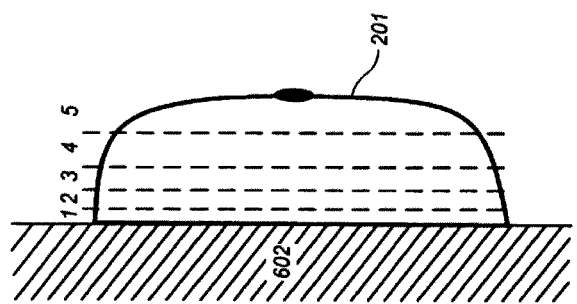
FIGS. 6A and 6B illustrate a side view of a breast and an example of different slab-like coronal subvolume thickness schemes according to a preferred embodiment.
Figure 6B:
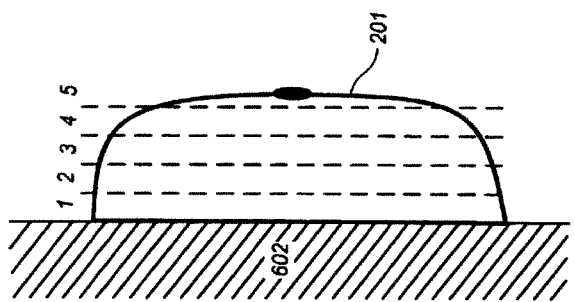

FIGS. 6A and 6B illustrate side views of a breast 210 next to a chest wall 602 for the purpose of describing coronal slab-like subvolume thickness schemes according to the preferred embodiments. In the preferred embodiment of FIG. 6A, the thicknesses of coronal slab-like subvolumes 1-5 are substantially equal. However, in the preferred embodiment of FIG. 6B, there is a graded or phased approach to the thicknesses of coronal slab-like subvolumes 1-5. More particularly, the inner subvolumes 1-2 are thinner than the outer subvolumes 4-5. Thus, an average thickness of a first subset of said slab-like subvolumes located closer to the chest wall is less than an average thickness of a second subset of said slab-like subvolumes located farther from the chest wall.

The graded or phased approach of FIG. 6B has been found advantageous because a large percentage of breast lesions are nearby to the chest wall, and so a more precise viewing of these tissues (i.e., approaching the precision of conventional thin-slice ultrasound images) is warranted. At the same time, however, it is still desirable to avoid "too much information" on the user display, and so thicker subvolumes for the regions farther away from the chest wall are used to keep the overall number of required images at manageable levels.

Figure 7:
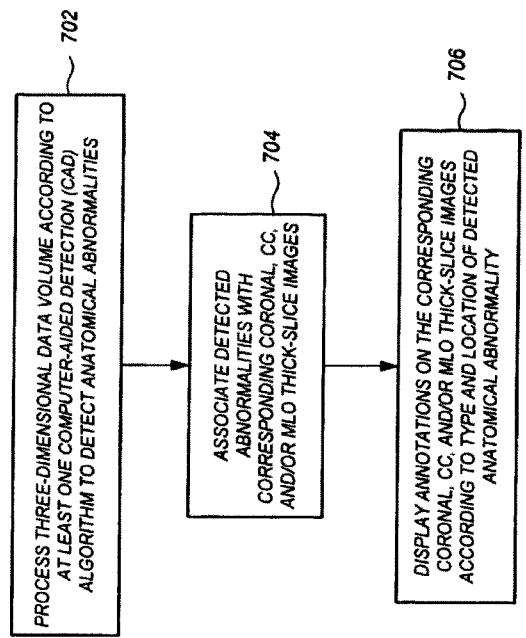
FIG. 7 illustrates a method for processing and displaying breast ultrasound information according to a preferred embodiment.

FIG. 7 illustrates a method for processing and displaying breast ultrasound information according to a preferred embodiment. At step 702, the three-dimensional data volume is processed according to at least one computer-aided detection (CAD) algorithm to detect anatomical abnormalities therein. These CAD algorithms can be the same as used supra for enhancing the visual appearance of lesions in the thick-slice images, or alternatively can be different and/or additional CAD algorithms. At step 704, the detected lesions in the three-dimensional data volume are mapped into their corresponding coronal thick-slice images. The detected lesions are also mapped into their corresponding CC and/or MLO thick-slice images if present. At step 706, annotations are superimposed on the corresponding coronal, CC, and/or MLO thick-slice images according to type and location of detected anatomical abnormality.

Figure 8:
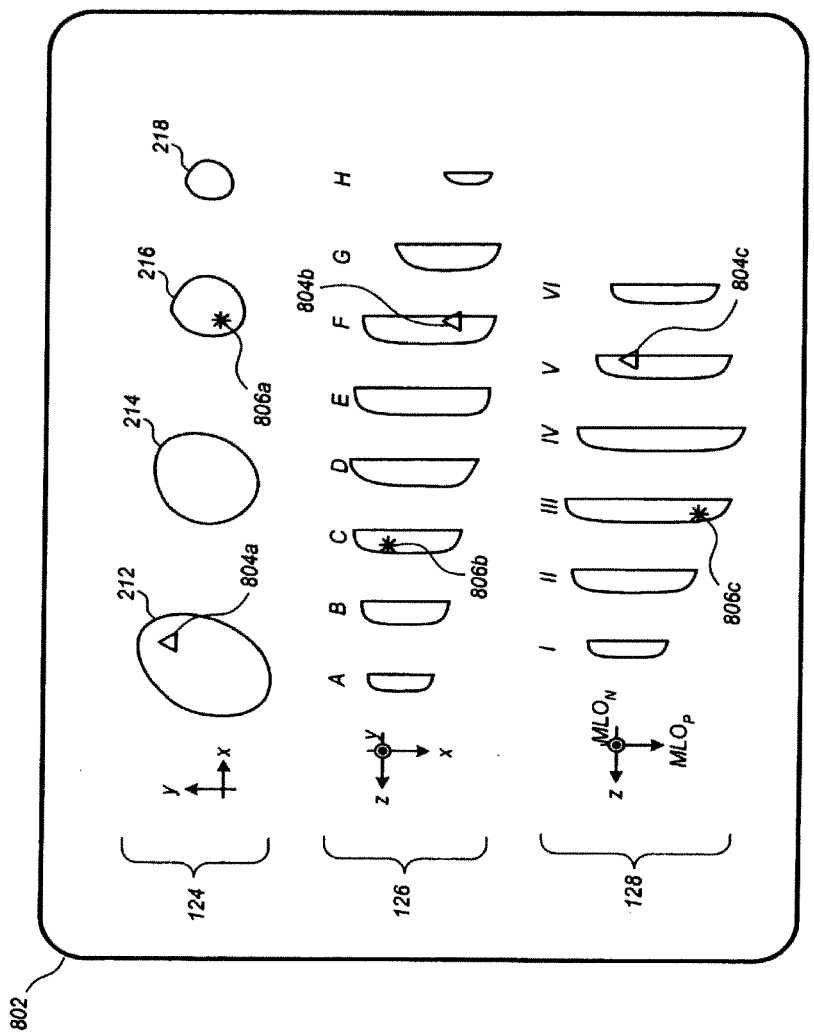
FIG. 8 illustrates a user display according to a preferred embodiment.

FIG. 8 illustrates a viewing workstation 802 according to a preferred embodiment, which is similar to the viewing workstation 122 but also includes CAD annotations on the coronal, CC, and MLO thick-slice images. The CAD annotations are placed according to type and location of detected anatomical abnormality. In the example of FIG. 8, a CAD-detected suspicious microcalcification cluster is denoted by triangles 804a, 804b, and 804c on the appropriate members of the coronal, CC, and MLO thick-slice image arrays, respectively. A CAD-detected suspicious mass is denoted by asterisk-shaped markers 806a, 806b, and 806c on the appropriate members of the coronal, CC, and MLO thick-slice image arrays, respectively.

Figure 9:
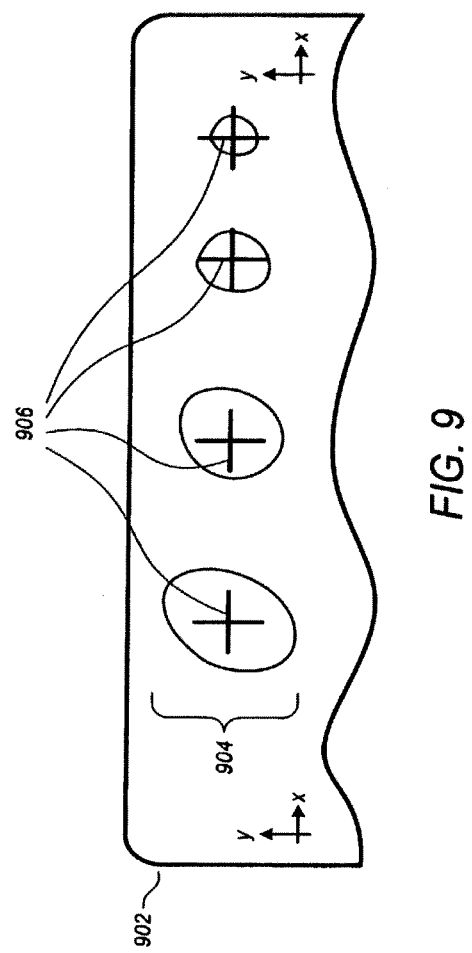
FIG. 9 illustrates a user display according to a preferred embodiment.

FIG. 9 illustrates a portion 902 of a viewing workstation according to a preferred embodiment, including an array 904 of coronal thick-slice images. It has been found useful to identify the x-y location of the nipple relative to the coronal thick-slice images on the user display, as indicated by the nipple markers 906. For example, it will not always be the case that the nipple will be at the center of each coronal thick-slice image, for anatomical reasons as well as the fact that there may be variations in the angle of attack of the chestward compressive force on the breast. These variations in the angle of attack may be unintentional, as in the case of imperfect patient positioning, or may be intentional, as in the case where a particular area of the breast (e.g., the upper inner quadrant) may be of concern in a follow-up scan. The position of the nipple can be determined using CAD algorithms on the three-dimensional data volume based on nipple shadow effects. Alternatively, the nipple position may be identified manually by the technician at the time of scanning, e.g., by ensuring that the nipple falls on a predetermined point on the compression plate, or by interacting with the scanning system based on a quick exploratory sweep across the breast by the probe, or by manually positioning the probe at the nipple location and pressing a nipple identification button, or by any of a variety of other manual nipple identification schemes.

Figure 10:
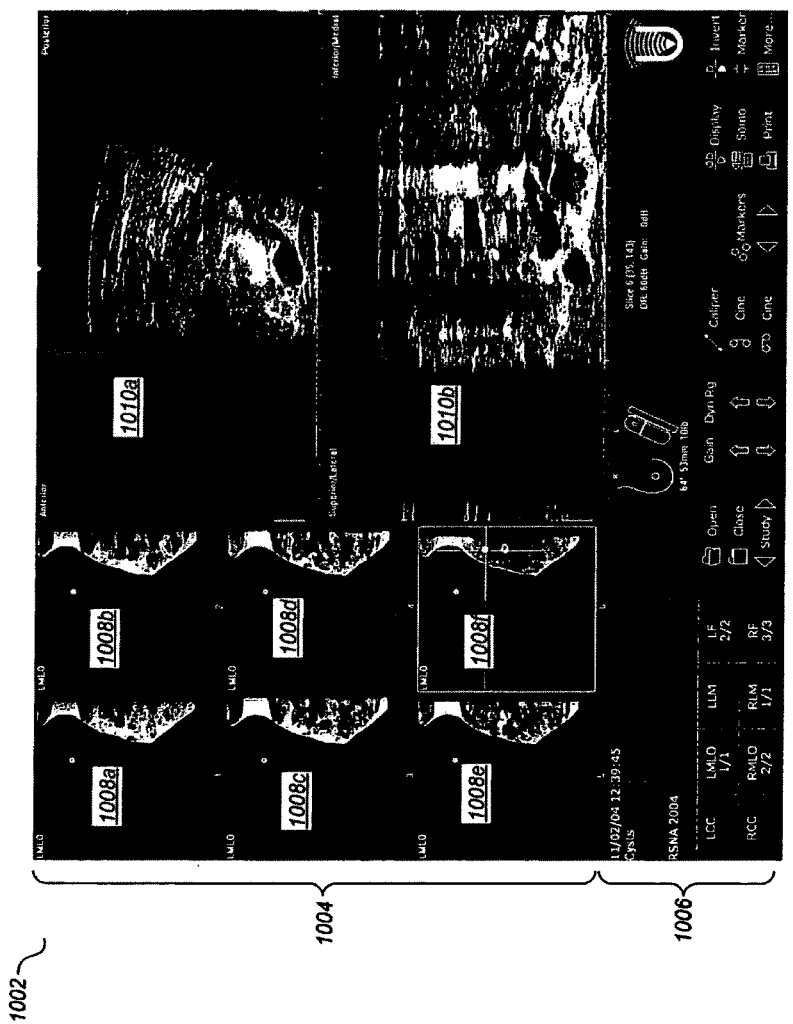
FIG. 10 illustrates a breast ultrasound display according to a preferred embodiment.

FIG. 10 illustrates a breast ultrasound display 1002 according to a preferred embodiment, generally comprising an image area 1004 and a menu bar 1006. In the particular display of FIG. 10, an array of six thick-slice images 1008a-1008e is displayed, as well as two planar ultrasound images 1010a-1010b. The display 1002 can be used in the viewing workstation 122 of FIG. 1, supra. The display 1002 can be used as part of a multi-modality PACS workstation, as a stand-alone device, and/or in conjunction with an x-ray mammography softcopy or hardcopy (i.e., lightbox) viewing station.

FIG. 11 illustrates a closer view of the menu bar 1006 comprising a variety of controls and information displays relating to the image area 1004. Menu bar 1006 comprises a body marker icon 1102, cine control (soft) buttons 1103, a marker display button 1104, marker navigation buttons 1106, a bilateral comparison control button 1108, a somogram button 1110, an invert button 1112, and a variety of file control buttons 1114. A designation of "/N" (N=2, 3, . . . ) on a view-related one of the file control buttons 1114 indicates that N sets of data are available for display for that view, e.g., N scans were taken corresponding to that view. The number preceding the "/N" denotes which of those sets is being displayed.

The cine control buttons 1103 allow the viewer to start a slice-by-slice ultrasound view cine loop sequence of the current breast view. It will start at the current cursor location, moving toward a first edge of the breast volume. It will delay there for a short period of time, then restart at the other edge of the breast volume. Pressing any button or moving the mouse while the cine is active will stop the cine loop, leaving the cursor at its most recent cine position. The invert button 1112 enables toggling of the thick-slice images between two different grayscale mapping modes, one for a generally white-on-black image mode, and another for a generally black-on-white image mode.

The bilateral comparison control button 1108 allows the viewer to dynamically toggle between displaying a bilateral comparison view format, as described further infra with respect to FIGS. 15-16 and FIGS. 19-20, or thick-slice views of a single breast. The somogram button 1110 allows the viewer to toggle between a first configuration in which only planar views are shown, a second configuration in which only thick-slice images are shown, and a third configuration in which combinations of thick-slice images and planar images are shown.

The marker display button 1104 allows the viewer to toggle between (i) non-annotated versions of the displayed images, and (ii) versions showing bookmarks as described further infra. The marker navigation buttons 1106 allow the viewer to perform bookmark-centric navigation wherein, upon selection, there is automatically displayed a corresponding one of the thick-slice images associated with a location of a next bookmark (forward) or prior bookmark (backward), as well as a one or more planar ultrasound images corresponding to that location. The bookmarks themselves may be entered by the viewer using a simple right-click and pull-down menu process, although the scope of the preferred embodiments is not so limited. By way of example, bookmarks may be provided by other users, automatically generated according to archived data, or by any of a variety of other processes.

Although not shown in FIG. 11, in another preferred embodiment there is provided a CAD display button and CAD navigation buttons providing similar navigational functionality as the marker display button 1104 and the marker navigation buttons 1106. In still another preferred embodiment, a nipple marker display button is provided for toggling between displaying nipple markers, described further infra, and not displaying nipple markers.

Body marker icon 1102 is automatically generated and provides fast communication of several different aspects of the images being displayed. A text section 1116 communicates a compression angle (for non-frontal, i.e., non-coronal, compression planes such as CC, MLO, LAT, etc.), a separation distance between compression plates (again for non-frontal compression planes), and a compression force used during the scans. The body marker icon 1102 further displays a compression plane 1117 against which the breast was compressed, a thick-slice depth marker 1118 corresponding to the depth of the displayed thick-slice image (when one thick-slice image is displayed), and a plane marker 1120 corresponding to a planar ultrasound image being displayed, if applicable.

FIG. 12 illustrates body marker icons for various non-frontal compression scenarios. The body marker icon 1202 corresponds to a LAT view of the right breast, the body marker icon 1204 corresponds to a CC view of the right breast, and the body marker icon 1206 corresponds to an MLO view of the left breast.

FIG. 13 illustrates body marker icons 1302, 1304, and 1306 for various frontal compression scenarios, each comprising a probe sweep indicator (e.g., 1303) indicating a trajectory and orientation of the linear scanning probe that scanned the breast. The body marker icon 1302 corresponds to a frontal scan of a medial side of the left breast in the inferior-to-superior direction, the body marker icon 1306 corresponds to a frontal scan of a medial side of the right breast in a direction close to the inferior-to-superior direction, and the body marker icon 1304 corresponds to a frontal scan of the center area of the left breast in a direction close to a lateral-to-medial direction.

Figure 14:
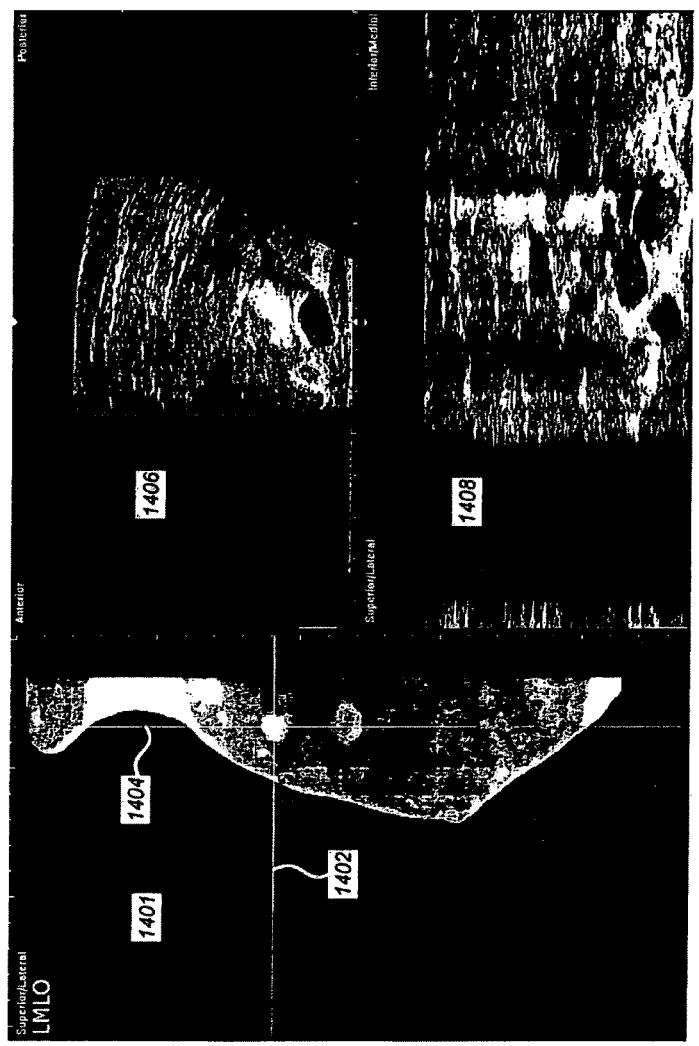
FIG. 14 illustrates a thick-slice image and planar views according to a preferred embodiment.

FIG. 14 illustrates a single thick-slice image 1401, which corresponds to the thick-slice image 1008f when the cursor is clicked at the location indicated in FIG. 10. It is to be appreciated that the menu bar 1006 is preferably displayed below all images but is omitted in this and subsequent figures for clarity. FIG. 14 further illustrates planar ultrasound images 1406 and 1408 corresponding respectively to the plane indicators 1402 and 1404, which intersect at the current cursor location.

Figure 15:
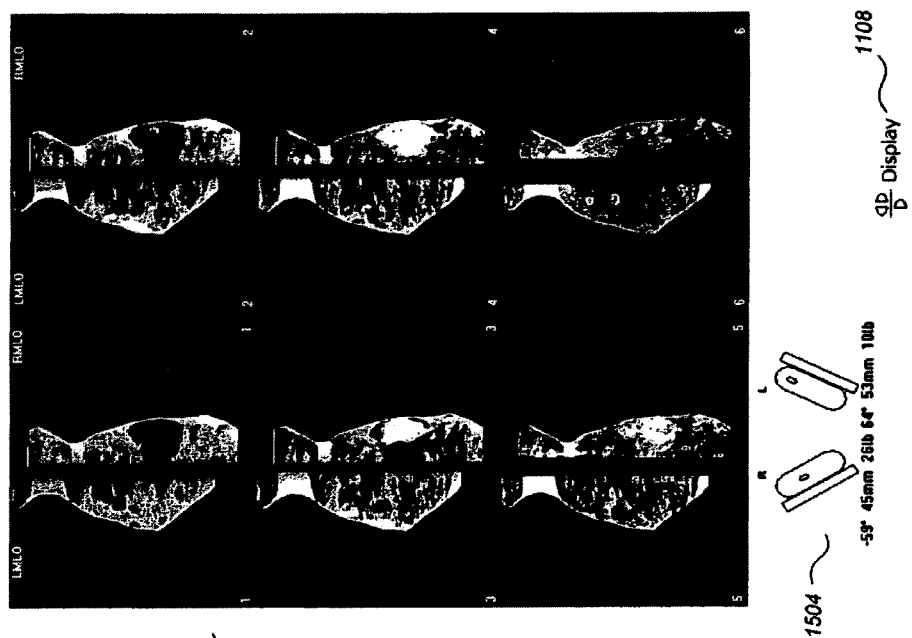
FIG. 15 illustrates a bilateral comparison array of thick-slice images, corresponding body marker icons, and a display control button according to a preferred embodiment.

FIG. 15 illustrates a bilateral comparison array 1502 of thick-slice images that is accessed by selection of the bilateral comparison control button 1108, comprising members of an LMLO thick-slice image array as positionally paired with corresponding members of an RMLO thick-slice image array, wherein the slab-like subvolumes of the left breast corresponding to the LMLO thick-slice image array have an at least general positionwise association with the slab-like subvolumes of the right breast corresponding to the RMLO thick-slice image array. A body marker icon 1504 illustrates the scanning orientations and other scanning parameters associated with each of the volumetric scans.

Figure 16:
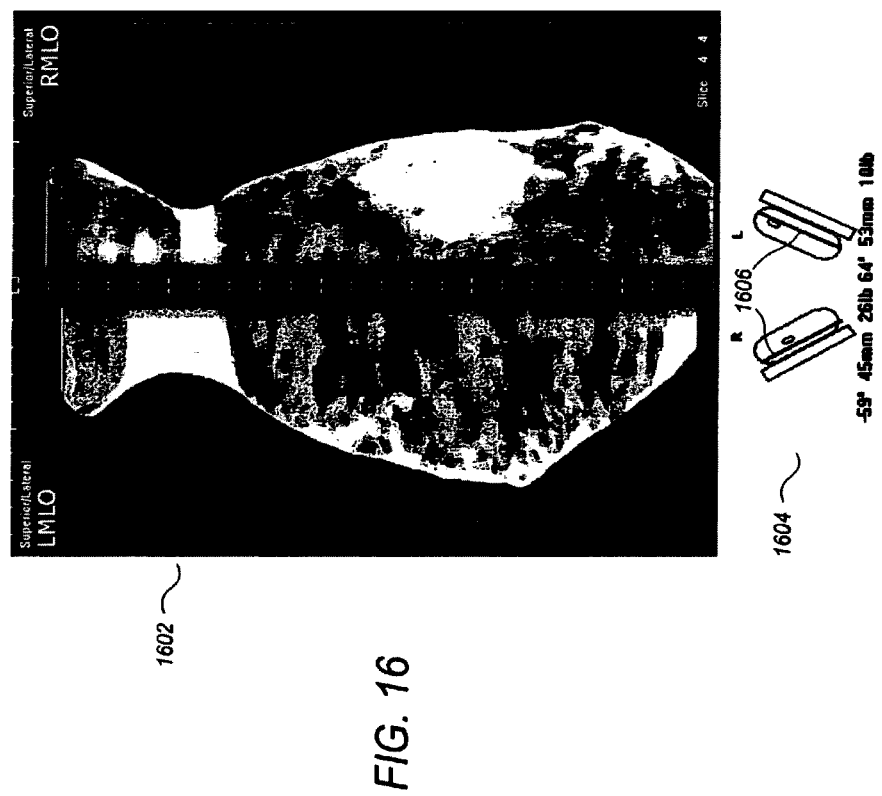
FIG. 16 illustrates a bilateral comparison view of thick-slice images and corresponding body marker icons according to a preferred embodiment.

FIG. 16 illustrates an expanded bilateral comparison view 1602 of the fourth thick-slice image pair of the bilateral comparison array 1502, which is displayed to when either of those fourth thick-slice images is clicked by the viewer on the display of FIG. 15. A body marker icon 1604 includes thick-slice depth markers 1606 showing the location of the fourth thick-slice subvolume within each of the left and right breasts. Nipple locations are also indicated on the body marker icon 1602.

Notably, it is not required that the associations between slab-like subvolumes of the left and right breasts be precise for the preferred embodiments of FIGS. 15-16. The opposing breasts can be of different sizes and there can be many incidental variations between the ways they were scanned. Nevertheless, it has been found highly useful to present thick-slice image data in bilateral comparison formats such as those of FIGS. 15-16. For example, breast symmetry is readily analyzed.

Figure 17:
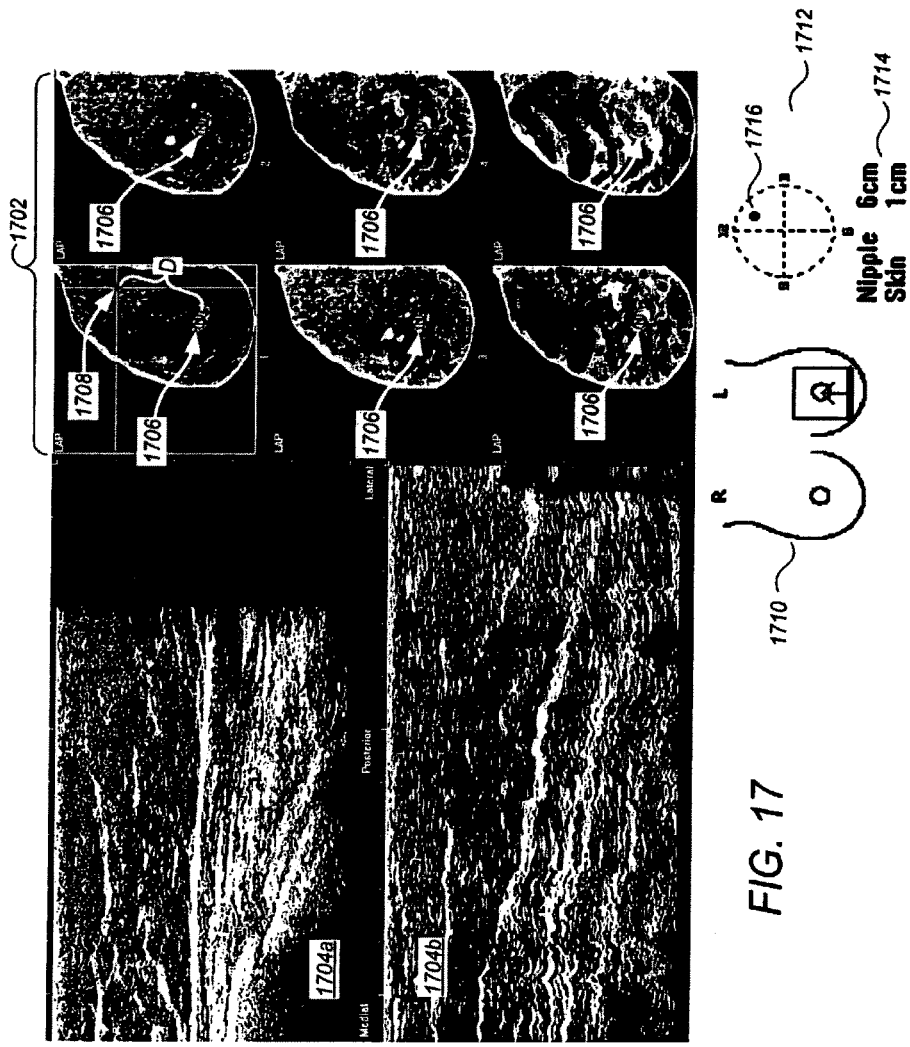
FIG. 17 illustrates an array of thick-slice images with nipple markers, a body marker icon, and a frontal breast icon according to a preferred embodiment.

FIG. 17 illustrates an array of thick-slice images 1702, two planar images 1704a-b corresponding to a current cursor position 1708 on a selected thick-slice image, a body marker icon 1710, nipple markers 1706, and a frontal breast icon 1712 according to a preferred embodiment. The nipple markers 1706 can be placed on the thick-slice images according to any of (i) a manually-entered nipple position provided with the associated volumetric ultrasound scan, (ii) a computer-derived nipple position automatically generated from the associated volumetric ultrasound scan, (iii) a computer-derived nipple position automatically generated based on manual placement of a physical nipple token for the associated volumetric ultrasound scan, and (iv) a viewer-determined position for the nipple marker. Physical nipple token can refer to a marker placed on the skin of the breast at the nipple location that is at least partially transparent to ultrasound but that also provides a degree of obscuration sufficient for automatic identification of its presence. Examples can include small silicone toroids, optionally with specks of metal therein, or any of a variety of other objects that can have similar effects. Physical nipple token can alternatively refer to a such a marker placed on the ultrasound scanning device itself, e.g., on one of the compression plates, at the nipple location.

Frontal breast icon 1712 comprises a cursor position indicator 1716 variably disposed thereon in a manner that reflects a relative position between the cursor 1708 and the nipple marker 1706 on the selected thick-slice image. Preferably, the frontal breast icon 1712 has a layout at least roughly resembling a clock face, and the cursor position indicator 1716 is positioned relative to the center of that clock face to reflect both (i) the distance "D" between the cursor 1708 and the nipple marker 1706, and (ii) the direction of the cursor 1708 from the nipple marker 1706 on the display (e.g., about 1:00 in the example of FIG. 17). The location of the cursor position indicator 1716 dynamically moves on the clock face as the cursor 1708 is moved around the thick-slice image. The combined display of the frontal breast icon 1712 and the body marker icon 1710 facilitates quick, intuitive comprehension of the physical and positional relevance of the images being displayed. Frontal breast icon 1712 further comprises a text portion 1714 numerically indicating (i) the distance "D," and (ii) the depth of the currently selected thick-slice image from the compressed surface across which the ultrasound probe was swept.

Figure 18:
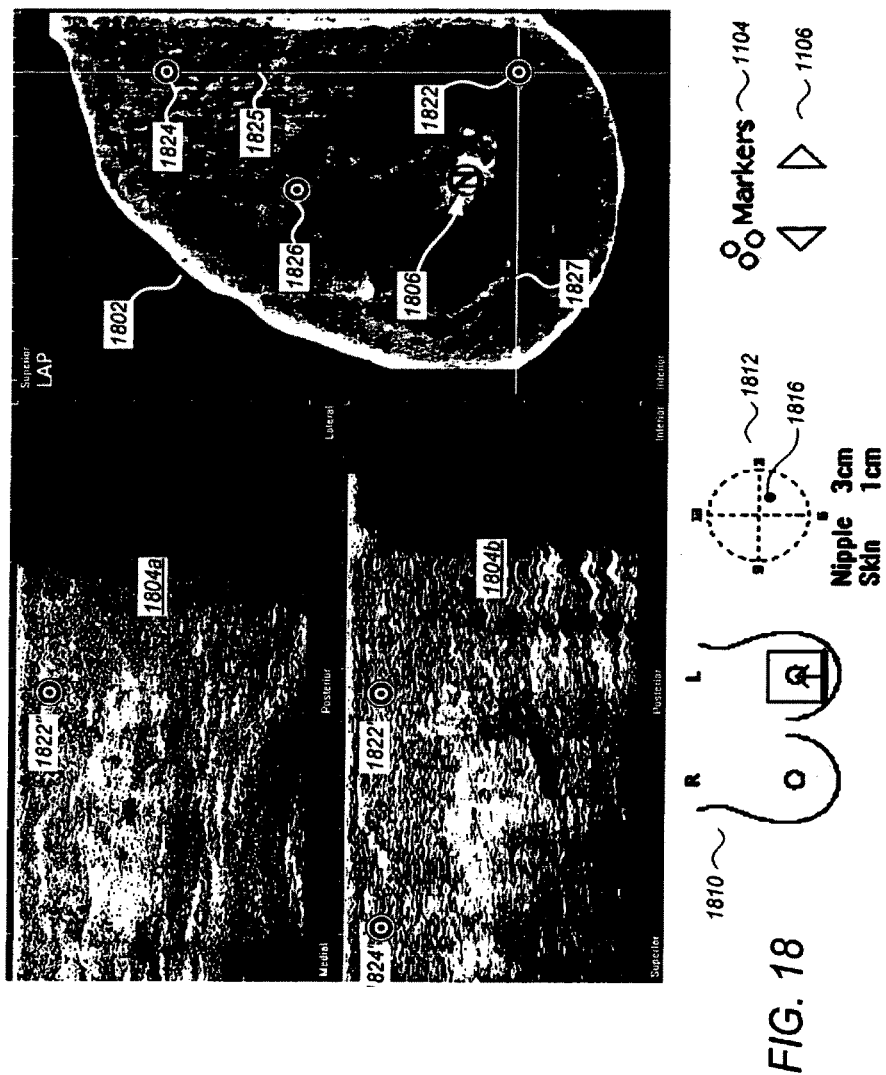
FIG. 18 illustrates a thick-slice image and planar images with displayed bookmarks, a body marker icon, a frontal breast icon, a marker display button, and marker navigation buttons according to a preferred embodiment.

FIG. 18 illustrates a thick-slice image 1802, two planar images 1804a-b corresponding to a current cursor position on the thick-slice image, a body marker icon 1810, nipple markers 1806, a plurality of bookmarks 1822, 1824, and 1826, and a frontal breast icon 1812. According to a preferred embodiment, the bookmarks are projected onto corresponding locations of the currently displayed planar images 1804a-b, if applicable, under an assumption that the bookmark spot is volumetrically in the middle plane of the slab-like subvolume corresponding to the thick-slice image. Accordingly, FIG. 18 illustrates corresponding bookmarks 1822' and 1824' on the superior-inferior planar image 1804b, because the bookmarks 1822 and 1824 lie along the vertical plane indicator 1825 passing through the current cursor location. The medial-lateral planar image 1804a only shows a corresponding bookmark 1822" because only the bookmark 1822 lies along the horizontal plane indicator 1827. Since neither plane indicator 1825 or 1827 intersects the bookmark 1826, there is no corresponding bookmark on the planar images 1804a-b for that bookmark.

The presence of all of the bookmarks can be toggled on and off by pressing the marker display button 1104. The marker navigation buttons 1106 allow the viewer to perform bookmark-centric navigation wherein, upon selection, the cursor is moved to a next bookmark (forward) or prior bookmark (backward), and the corresponding planar images are instantly displayed. As a default setting, navigation among the bookmarks is ordered in the same order as the bookmarks were entered by the viewer, although the scope of the preferred embodiments is not so limited. In the example of FIG. 18, the viewer has just pressed the one of the marker navigation buttons and has landed at the bookmark 1822. Notably, as indicated by the cursor position indicator 1816, the frontal breast icon 1812 keeps up automatically with the current cursor position, which in FIG. 18 is about 3 cm from the nipple marker location at a clock angle of roughly 4:00. The nipple markers and bookmarks can have any of a variety of shapes, sizes, colors, etc. without departing from the scope of the preferred embodiments.

FIG. 19 illustrates an array of thick-slice images 1902 with nipple markers 1906 that have been shifted by the viewer (using a click-and-drag method, for example). Although not necessarily warranted in this example (because the original position appears accurate based on nipple shadow positions), it may be desirable for the viewer to move the nipple marker location based on their observations, or on other extrinsic information. The position of the cursor 1908 relative to the nipple marker 1906 having shifted, the position of the cursor position indicator 1916 automatically shifts on the clock face of the frontal breast icon from 1916-old to 1916-new (e.g., from about 0.5 cm at 12:00 to about 3 cm at 4:00).

FIG. 20 illustrates an array of thick-slice images 2002 with bookmarks 2010, 2011, 2012, and 2013 placed thereon, for illustrating a multi-slice bookmark-centric navigation process according to a preferred embodiment. By the viewer clicking on the forward marker navigation button 1106, the cursor is instantly taken to the next bookmark, and corresponding planar images (not shown) are displayed.

Generally speaking, as in the example of FIG. 20, there will often be bookmarks on several of the thick-slice images. Convenient navigation analogous to that shown in FIG. 20 is provided when only one of the thick-slice images is displayed at a time (see, e.g., FIG. 14, supra). In particular, when only a single thick-slice image is being shown and one of the marker navigation buttons 1106 is pressed, the current thick-slice image is replaced (if applicable) with a next thick-slice image corresponding to a next bookmark, and the cursor is placed at the next bookmark in that thick-slice image with corresponding planar views being displayed. Rapid navigation among bookmarks is thereby achieved.

In another preferred embodiment, similar navigation capabilities are provided among CAD detections, i.e., by the viewer clicking on a CAD navigation button, the cursor is instantly taken to the next CAD marker location, and corresponding planar images are displayed. Among other advantages, bookmark-centric and/or CAD-centric navigation according to the preferred embodiments can substantially reduce the time needed to examine a case and increase radiologist productivity.

FIG. 21 illustrates breast ultrasound volume processing and display according a preferred embodiment. At step 2102, nipple position is obtained either manually or in an automated manner relative to an acquired breast volume that is preferably chestwardly-compressed for head-on scanning. At step 2104, one or more thick-slice ultrasound images is displayed. At step 2106, nipple markers are shown on the thick-slice image(s), the nipple marker positions representing a projection of the nipple location thereupon. At step 2108, the current cursor position relative to the displayed nipple marker position is communicated on a clock face style icon. At step 2110, the viewer is allowed to change the nipple marker position relative to the breast volume through direct interaction on thick-slice image(s).

FIG. 22 illustrates breast ultrasound volume processing and display according a preferred embodiment. At step 2202, bookmarks are added via bookmarking commands, e.g., through a right-click and drop-down menu style command upon a thick-slice image or a planar image. At step 2204, that bookmark location is associated with its corresponding location within the 3D breast volume. At step 2206, that bookmark is projected onto all relevant displayed thick-slice and planar ultrasound images as required to properly reflect its position in the 3D breast volume. If a marker navigation command is received at step 2208, then the display automatically navigates to a next bookmark location and shows the appropriate thick-slice image and corresponding planar images at step 2210.

Figure 23:
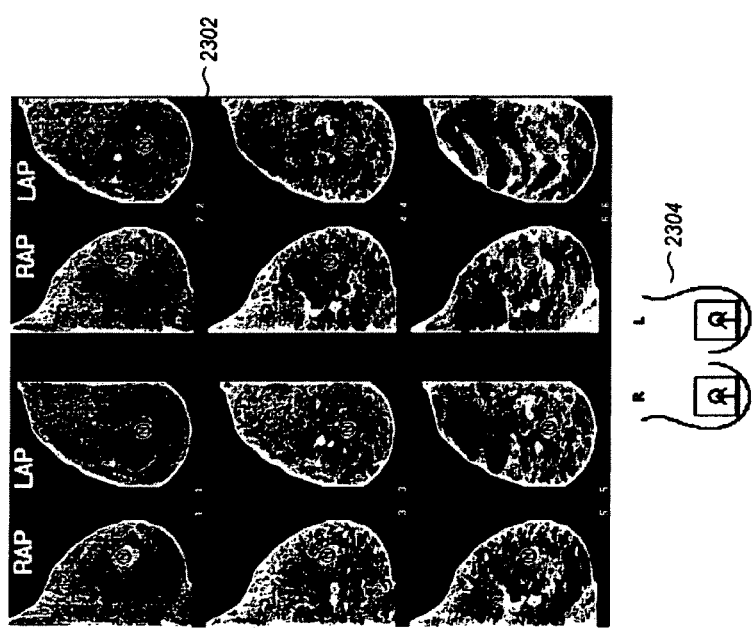
FIG. 23 illustrates a bilateral comparison array view of thick-slice images and corresponding body marker icons according to a preferred embodiment.

FIG. 23 illustrates a bilateral comparison array 2302 of thick-slice images that is easily navigated to by selection of the bilateral comparison control button 1108, supra, comprising members of an LAP (left anterior-posterior) thick-slice image array as positionally paired with corresponding members of an RAP (right anterior-posterior) thick-slice image array, wherein the slab-like subvolumes of the left breast corresponding to the LAP thick-slice image array have an at least general positionwise association with the slab-like subvolumes of the right breast corresponding to the RAP thick-slice image array. A body marker icon 2304 illustrates the scanning orientations for each breast volume.

Figure 24:
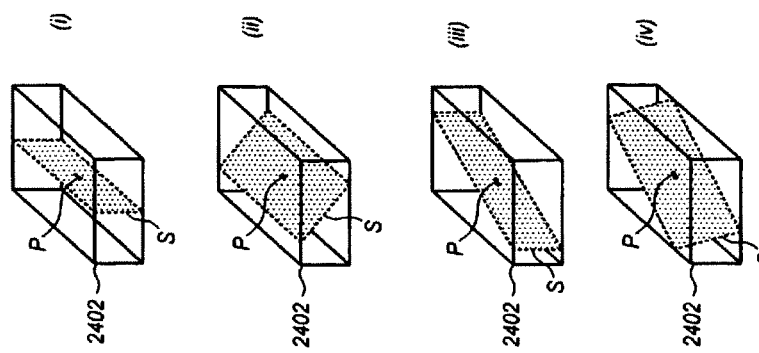
FIG. 24 illustrates examples of virtual probe reconstruction planes according to a preferred embodiment.

FIG. 24 illustrates examples of a virtual probe reconstruction (VPR) plane "S" around a point "P" within a breast volume 2402 according to a preferred embodiment. The viewer is provided with a pointing device, which can be the regular mouse in a particular mode, or which can be a separate joystick or similar control. With at least one thick-slice image and at least one planar image being displayed, the viewer can invoke a VPR command for the present cursor position. This causes the cursor to freeze at the present location "P" within the breast volume, wherein the viewer can then change the orientation of the plane "S" corresponding to the displayed planar image from a normal "vertical" position within the breast volume, see FIG. 24 at (i), to any of a variety of different orientations under control of the pointing device. For example, as indicated in FIG. 24, there is provided a roll capability, see FIG. 24 at (ii), a yaw capability, see FIG. 24 at (iii), and combinations of roll and yaw, see FIG. 24 at (iv).

Figure 25:
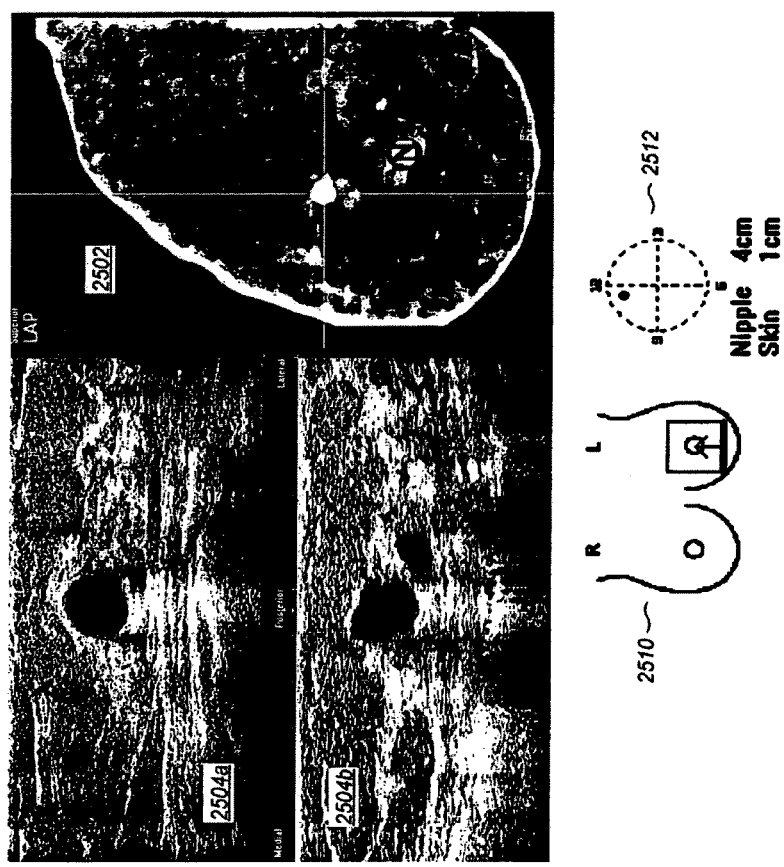
FIG. 25 illustrates a full-breast composite thick-slice image, a body marker icon, and a frontal breast icon according to a preferred embodiment.

FIG. 25 illustrates a full-breast composite thick-slice image 2502, corresponding planar images 2504a-b, a body marker icon 2510, and a frontal breast icon 2512 according to a preferred embodiment. Composite thick-slice image 2502 is preferably a CAD-enhanced expression of the sonographic properties of substantially the entire breast volume, i.e., all of the tissue imaged by the volumetric ultrasound scans. Any of a variety of CAD algorithms can be used such as those discussed U.S. Pat. No. 6,317,617, supra, and those described in the commonly assigned WO 03/101303 A1, supra. The lesions can then be enhanced according to their likelihood of malignancy (or other metric of interest) on the composite thick-slice image 2502. The composite thick-slice image 2502 can serve as a useful "guide" or "road map" for viewing the planar ultrasound images and the other thick-slice images, and can optionally be provided with explicit CAD markings near the enhanced lesion locations.

Figure 26:
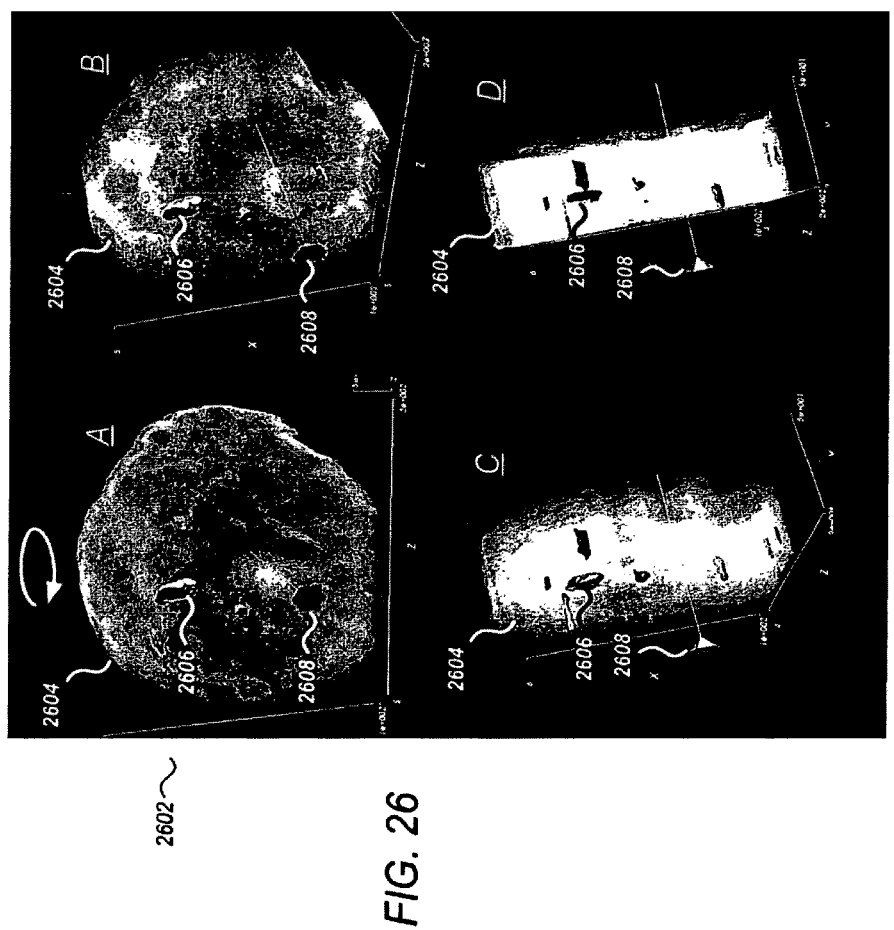
FIG. 26 illustrates a volume-rendered breast ultrasound volume with surface-rendered computer-assisted diagnosis (CAD) detections therein according to a preferred embodiment.

FIG. 26 illustrates a display 2602 comprising a volume-rendered breast ultrasound volume 2604 with surface-rendered computer-assisted diagnosis (CAD) detections 2606 therein according to a preferred embodiment. A three-dimensional nipple marker 2608 is provided to properly orient the viewer in visualizing the breast volume. In one preferred embodiment, the volume-rendered breast ultrasound volume 2604 is rotated in a cine-like fashion, as indicated by the sequence A-D in FIG. 26.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although primarily described supra in the context of ultrasound imaging, it is to be appreciated that data from other full-field breast imaging modalities (e.g., MRI, CT, PET) can be advantageously processed and displayed according to one or more of the described preferred embodiments. One or more of the displays described herein is similar to SOMOGRAM™ displays provided by U-Systems, Inc. of San Jose, Calif. By way of further example, although described supra as being volumetrically segregated, the coronal slab-like subvolumes from which the coronal thick-slice images are computed can be partially overlapping, which can be useful in dealing with lesions that would otherwise straddle the borders of the subvolumes. By way of even further example, although most nipple markers are described in the preferred embodiments supra in the context of coronal thick-slice images, in other preferred embodiments the nipple markers are shown on the MLO, CC, and other thick-slice image views.

By way of further example, it is to be appreciated that substantially parallel to a coronal plane is used herein to generally reflect the practical realities of situations such as head-on scanning of the breast, and that there may be some deviation from the plane of the chest wall. For example, for a particular patient having highly pendulous breasts it might be found most optimal to compress the breast at some small angle, such as 15 degrees, away from the plane of the chest wall. In this case, slab-like subvolumes that are taken parallel to the plane of compression would still be considered substantially parallel to the coronal plane.

By way of still further example, in alternative preferred embodiments the coronal slab-like subvolumes described supra can be replaced by thin-slice coronal images, i.e. thin-slice planar ultrasound images along planes substantially parallel to a coronal plane. This can be particularly useful in a follow-up diagnosis setting in which fine details are desired for viewing. By way of still further example, in another alternative preferred embodiment, the clinician is given the ability to interchangeably switch among, or pick-and-choose between, displaying the coronal slab-like subvolumes and the thin-slice coronal images. Therefore, reference to the details of the preferred embodiments are not intended to limit their scope, which is limited only by the scope of the claims set forth below.

Figure 27:
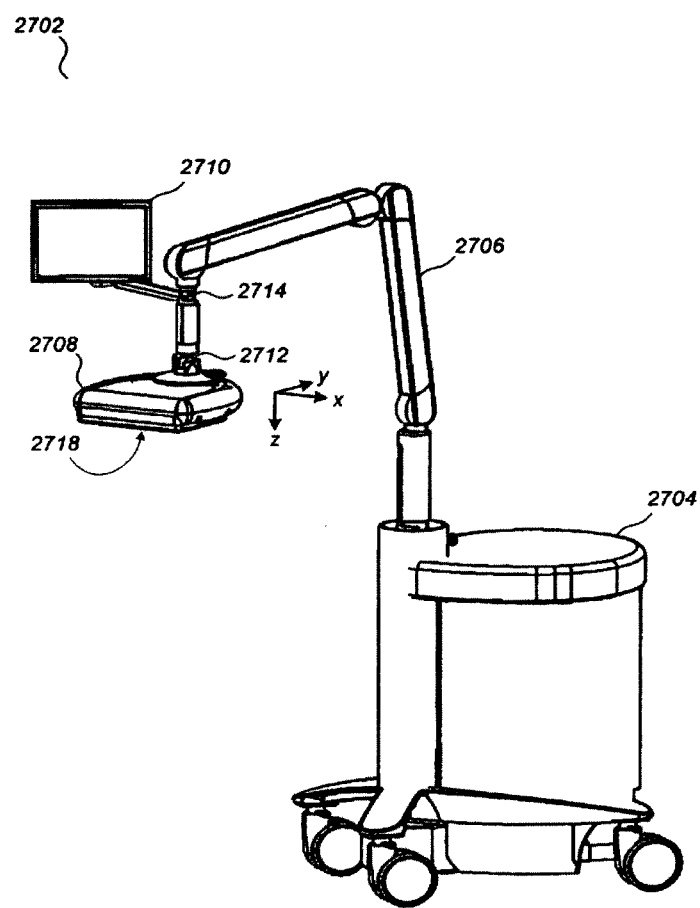

FIG. 27 illustrates a perspective view of a full-field breast ultrasound (FFBU) scanning apparatus 2702 according to a preferred embodiment, comprising a frame 2704 that may contain an ultrasound processor, a movable support arm 2706, a compression/scanning assembly 2708 connected to the support arm 2706 via a ball-and-socket connector 2712, and a monitor 2710 connected to the support arm 2706 at a joint 2714. Preferably, the support arm 2706 is configured and adapted such that the compression/scanning assembly 2708 is either (i) neutrally buoyant in space, or (ii) has a light net downward weight (e.g., 2-3 pounds) for breast compression, while allowing for easy user manipulation. According to a preferred embodiment, the compression/scanning assembly 2708 comprises an at least partially conformable membrane 2718 in a substantially taut state, the membrane 2718 having a bottom surface contacting the breast while a transducer is swept across a top surface thereof to scan the breast. Optionally, the support arm 2706 may comprise potentiometers (not shown) to allow position and orientation sensing for the compression/scanning assembly 2708, or other types of position and orientation sensing (e.g., gyroscopic, magnetic, optical) can be used. By way of example and not by way of limitation, a miniBIRD® 3D position sensor from Ascension Technologies can be used to determine the position and orientation of the compression/scanning assembly 2708 on a per-frame basis.

Within frame 2704 may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

The compression/scanning assembly 2708 is preferably a substantially self-contained, pod-like module that can be grasped by the hands of a user and manipulated to compress the breast in a generally chestward direction. By generally chestward, it is meant that membrane 2718 of the compression/scanning assembly 2708 urges the breast surface toward the chest wall of the patient while the membrane is an angle of 45 degrees or less from a coronal plane. It has been found that, generally speaking, the breasts of supine or reclining women can have many different tendencies depending on the anatomy of the woman. For example, for first fully supine woman the breast may droop upward toward the shoulder, while for a second fully supine woman the breast may droop downward toward the abdomen or inward toward the sternum. For these breasts it may be desirable to tilt the scanning surface somewhat relative to the coronal plane, obtaining a scan of the breast while pushing the breast at least partially sideways toward the theoretical center of the breast and while also pushing it inward toward the chest wall.

Notably, the scope of the preferred embodiments is not limited to the above-referenced angles relative to the coronal plane. In other preferred embodiments any of a variety of different angles and orientations may be used, depending on the circumstances.

Figure 28:
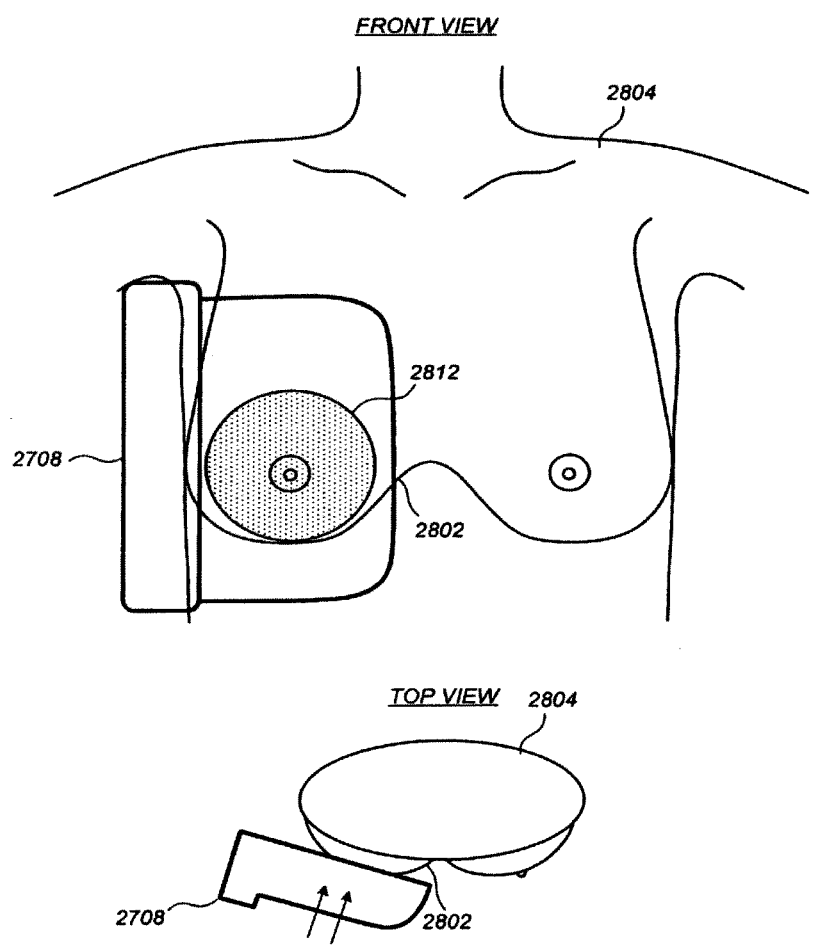
FIG. 28 illustrates a diagram of head-on breast ultrasound scanning according to a preferred embodiment.

FIG. 28 illustrates a diagram of head-on breast ultrasound scanning according to a preferred embodiment, in which a breast 2802 of a patient 2804 is scanned using the compression/scanning assembly 2708 of FIG. 12, supra. More generally any similar assembly having a substantially planar scanning surface that is rigid or semi-rigid as compared to the general softness of a breast can be used. For some clinical settings and/or patient groups, it is often considered sufficient to use a single head-on scan to volumetrically image a dense-disk region 2212 of the breast, the compressive surface being substantially parallel to the coronal plane and chestwardly pressed against the breast.

In other clinical settings and/or for other patient groups, it is often desired to more thoroughly scan the breast by obtaining ancillary compressive scans at one or more off-coronal angles. However, according to a preferred embodiment, at least some degree of systemization and/or standardization is maintained by using lateral frontal, medial frontal, inferior frontal, and/or superior frontal compression and scanning orientations as described herein. In one preferred embodiment, the image volumes acquired from the ancillary compressive scans are used to supplement the image volume acquired from the head-on scan. In another embodiment, the single head-on scans are omitted and only the image volumes acquired from the ancillary compressive scans are used.

Figure 29:
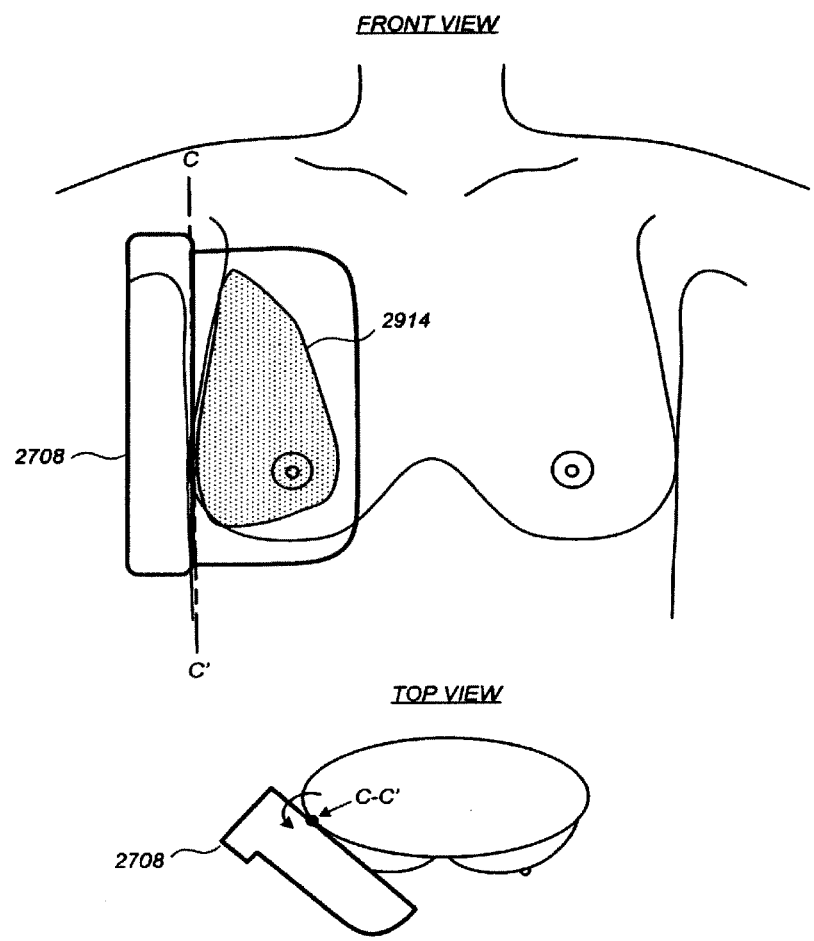
FIG. 29 illustrates a diagram of lateral frontal breast ultrasound scanning according to a preferred embodiment.

FIG. 29 illustrates a diagram of lateral frontal breast ultrasound scanning according to a preferred embodiment, in which the compression/scanning assembly 2708 is manipulated to image a lateral frontal region 2914. Preferably, in a positioning process preceding the probe sweep, one side of the compressive surface is pinned adjacent to the outer edge of the breast (near the line C-C' in FIG. 29) and then the compressive surface is "rolled" toward the medial side of the breast, until a position is reached in which the compressive surface would lift away from C-C' if the rolling continued. This has been found to allow capturing of a relatively large lateral frontal region 2914 that usually includes the nipple, while also minimizing small air pockets, bubbles, etc. that can degrade image quality.

Figure 30:
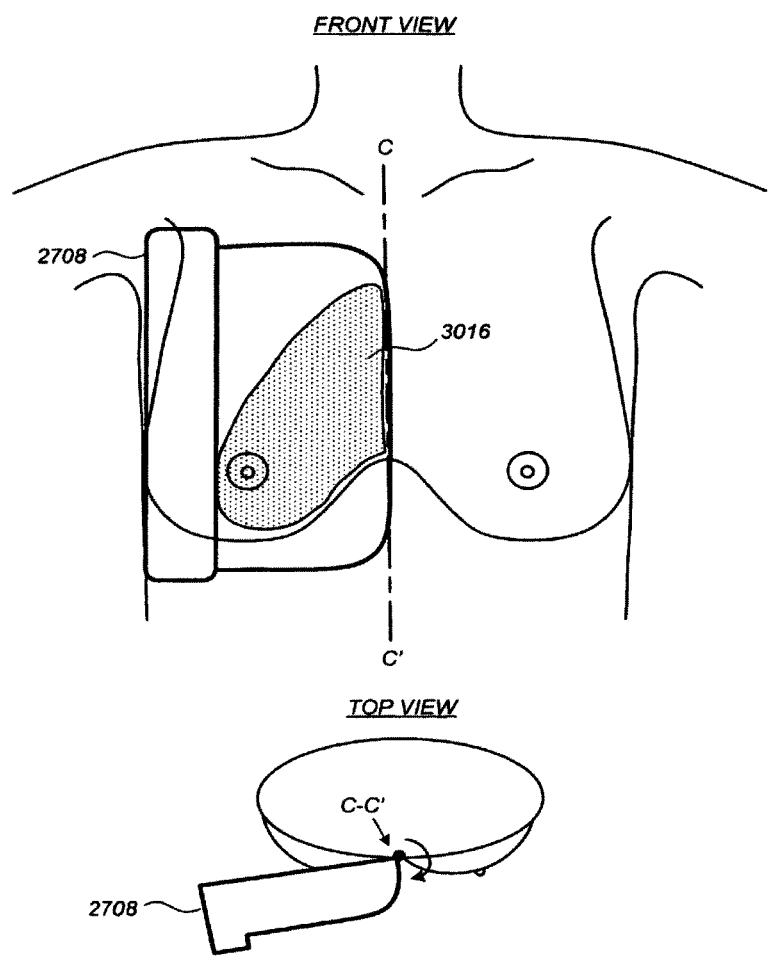
FIG. 30 illustrates a diagram of medial frontal breast ultrasound scanning according to a preferred embodiment.

FIG. 30 illustrates a diagram of medial frontal breast ultrasound scanning according to a preferred embodiment, in which the compression/scanning assembly 2708 is manipulated to image a medial frontal region 3016. In a manner analogous to the lateral frontal scan, one side of the compressive surface is preferably pinned adjacent to the medial edge of the breast (near the line C-C' in FIG. 30) and then the compressive surface is "rolled" toward the outer side of the breast, until a position is reached in which the compressive surface would lift away from C-C' if the rolling continued.

Figure 31:
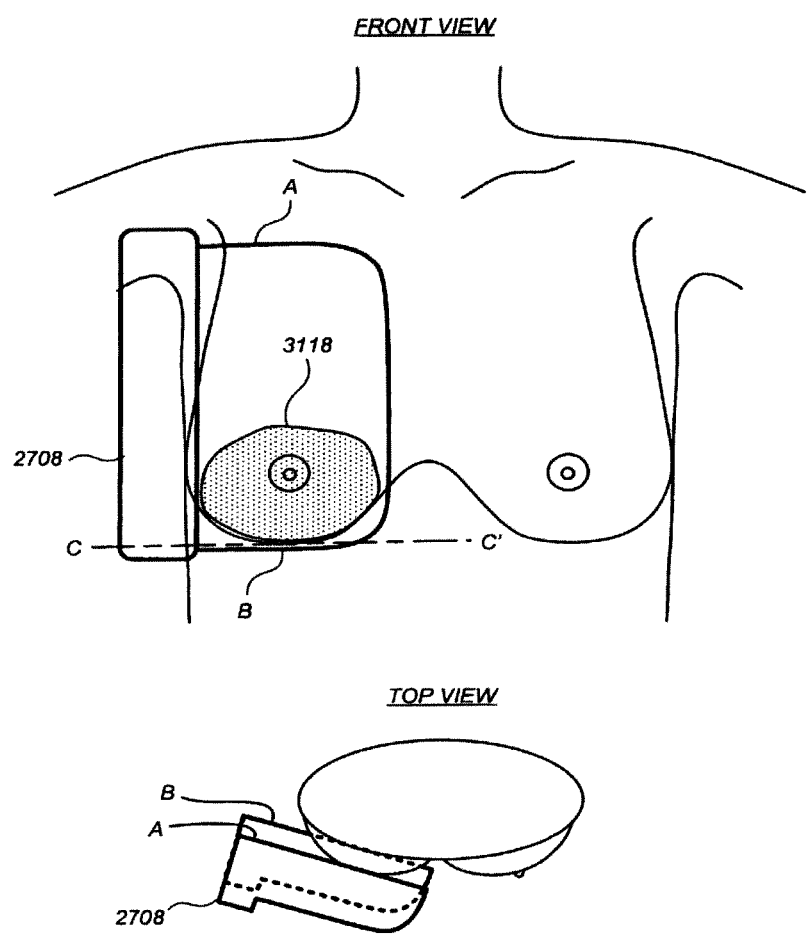
FIG. 31 illustrates a diagram of inferior frontal breast ultrasound scanning according to a preferred embodiment.
Figure 32:
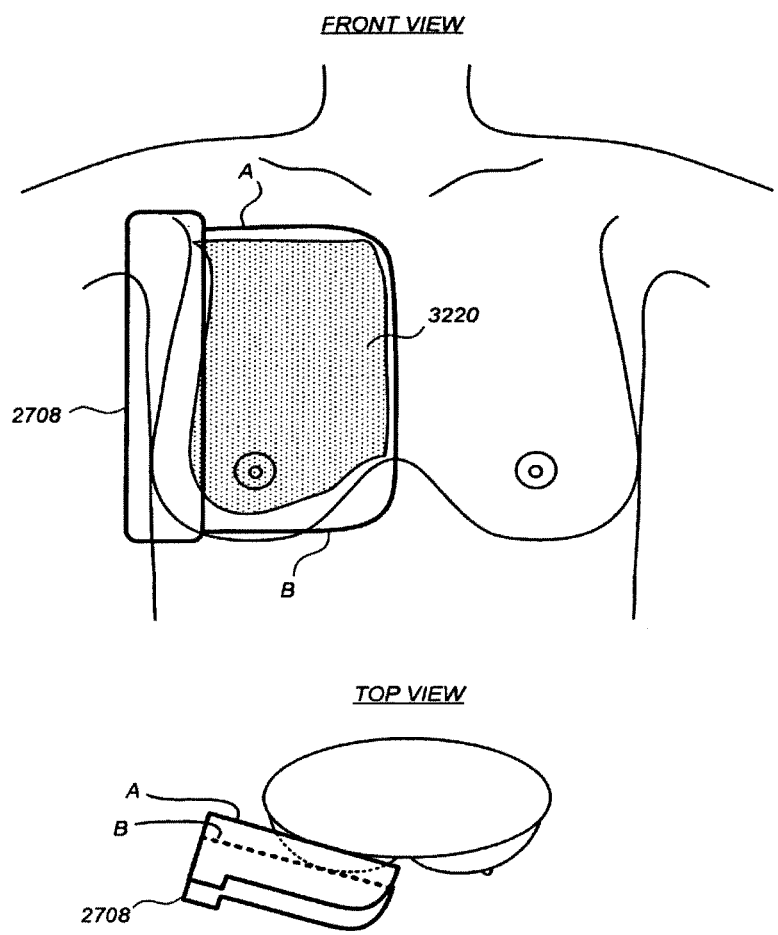
FIG. 32 illustrates a diagram of superior frontal breast ultrasound scanning according to a preferred embodiment.

FIG. 31 illustrates a diagram of inferior frontal breast ultrasound scanning according to a preferred embodiment, in which the compression/scanning assembly 2708 is manipulated to image an inferior frontal region 3118. In a manner analogous to the lateral and medial frontal scans, one side of the compressive surface is pinned at the inferior mammary fold (IMF, near the line C-C' in FIG. 31) and then the compressive surface is "rolled" upward toward the superior surface of the breast, until a position is reached in which the compressive surface would lift away from C-C' if the rolling continued. FIG. 32 illustrates a diagram of superior frontal breast ultrasound scanning according to a preferred embodiment, in which the compression/scanning assembly 2708 is manipulated to image a superior frontal region 3220.

In one embodiment, the number and selection of ancillary compressive scans is determined according to a size category of the breast. For a small breast, the lateral frontal scan (FIG. 29) and the medial frontal scan (FIG. 30) can suffice to ultrasonically image the clinically relevant tissues. For a medium sized breast, the inferior frontal scan (FIG. 31) is acquired in addition to the lateral and medial frontal scans to facilitate sufficient imaging of the clinically relevant tissues. For a large-sized breast, the superior frontal scan (FIG. 32) is acquired in addition to the lateral, medial, and inferior scans for capturing the clinically relevant tissues. Advantageously, a set of generally standard and comparable ultrasound image volumes is acquired according to the size of the breast for facilitating year-over-year comparisons, comparisons of similarly-sized breasts, and/or a variety of other useful purposes.

Figure 33:
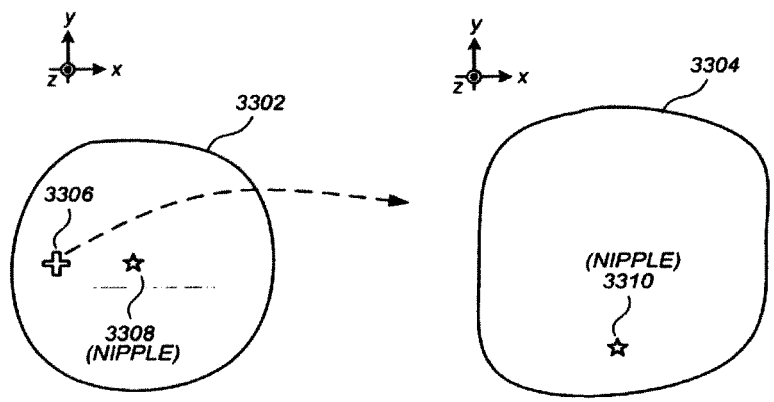
FIG. 33 illustrates thick-slice images from first and second breast ultrasound volumes and a region of interest (ROI) to be mapped from the first breast ultrasound volume to the second breast ultrasound volume according to a preferred embodiment.
Figure 34:
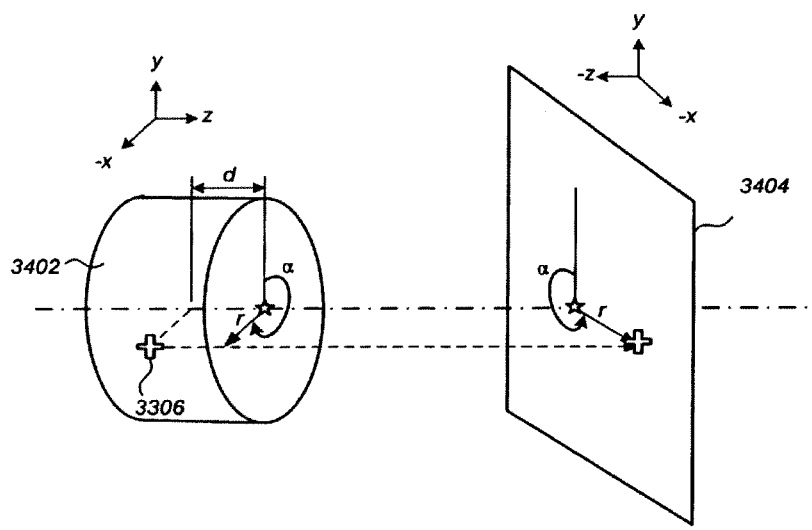
FIG. 34 illustrates a conceptual view of projection of a Cartesian offset from a nipple location in a first breast ultrasound volume to a coronal reference plane according to a preferred embodiment.

Automated navigation between a first ultrasonic volume of a breast acquired during a first volumetric scan thereof and a second ultrasonic volume of the same breast taken during a second volumetric scan thereof is now described. FIG. 33 illustrates one example of the overall goal of the method, showing a first coronal thick-slice image 3302 derived from a first ultrasound volume that may have been acquired according to FIG. 28, that is, a direct head-on scan. A second coronal thick-slice image 3304 is derived from a second ultrasound volume that may have been acquired according to FIG. 32, that is, a superior frontal scan. Alternatively, one or both of these images may be a planar ultrasound slice, the method proceeding in substantially the same way for planar slices as for thick-slice images. Generally speaking, the ultrasound display will segregate the images corresponding to the first and second ultrasonic volumes such that the viewer is aware of the distinction between the two. The user has selected a source region of interest (ROI) in the first image 3302, and according to a preferred embodiment, automatic navigation is provided by computing a corresponding location (termed a destination ROI) in the second thick-slice image and highlighting that location, allowing the user to quickly take a "different look" at the region of interest. The automated navigation is preferably nipple-centric, i.e., the mapping between volumes is based on a position of the source ROI relative to the nipple in the first ultrasonic volume, with the destination ROI being identified as that location in the second subvolume having the same relationship with the nipple location as it appears in the second subvolume. More particularly, the relative positions are based on distance and direction from the nipple when the ROI is projected onto a coronally oriented plane going through the nipple location. The described method has been found to yield sufficiently accurate results without requiring intensive internal feature-based volume mappings, while also being flexible for the large variety of different scan orientations that might be used.

Figure 37:
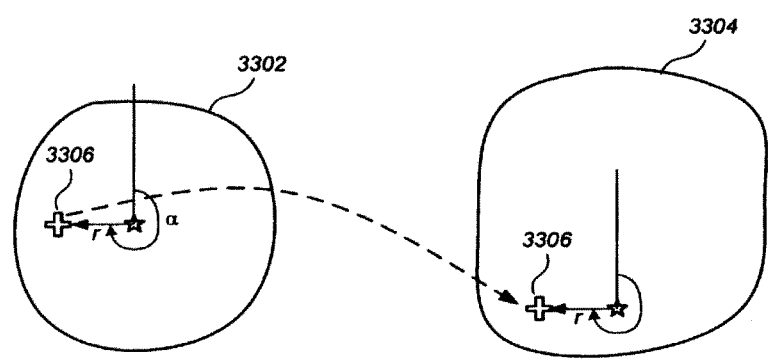
FIG. 37 illustrates the thick-slice images of FIG. 33 including a highlighted destination ROI according to a preferred embodiment.

Nipple locations 3308 and 3310 in the first and second ultrasonic volumes are identified either automatically or manually according to any of the above-described methods. Notably, the nipple is positioned directly in the middle for the head-on scan thick-slice image 3302 while it is skewed toward the bottom for the superior frontal scan thick-slice image 3304. When the ROI 3306 is selected (termed a source ROI herein), it is mapped from the thick-slice image 3302 into the corresponding first ultrasonic volume, according to the known position of the associated slab-like subvolume within the first ultrasonic volume. The source ROI is then mapped from within the first ultrasonic volume into a corresponding destination ROI within the second ultrasonic volume of the breast. The destination ROI is then mapped onto the second image 3304 according to the known position of the second thick-slice image within the second ultrasonic volume. The second image is displayed to the viewer with the position of the destination ROI therein being highlighted (see FIG. 37).

With reference herein to FIGS. 34-38, in one preferred embodiment, the mapping from the source ROI 3306 within the first ultrasonic volume 3402 into the corresponding destination ROI 3604 (see FIG. 36) within the second ultrasonic volume 3602 first comprises identifying a nipple location 3308 and 3310 of the breast in each of the first and second ultrasonic volumes 3306 and 3604. A projected location of the source ROI 3306 onto a first coronal reference plane 3404 passing through the nipple location within the first ultrasonic volume is then identified (see FIG. 34). A Cartesian offset (by Cartesian, it is meant that the offset is within a plane and can be identified by two coordinates such as $\Delta x$, $\Delta y$ or, in this case, a radius $r$ and angle $\alpha$; the term "in-plane offset" may alternatively be used) between the projected source ROI location and the nipple location on the first coronal reference plane 3404 is then determined.

Figure 35:
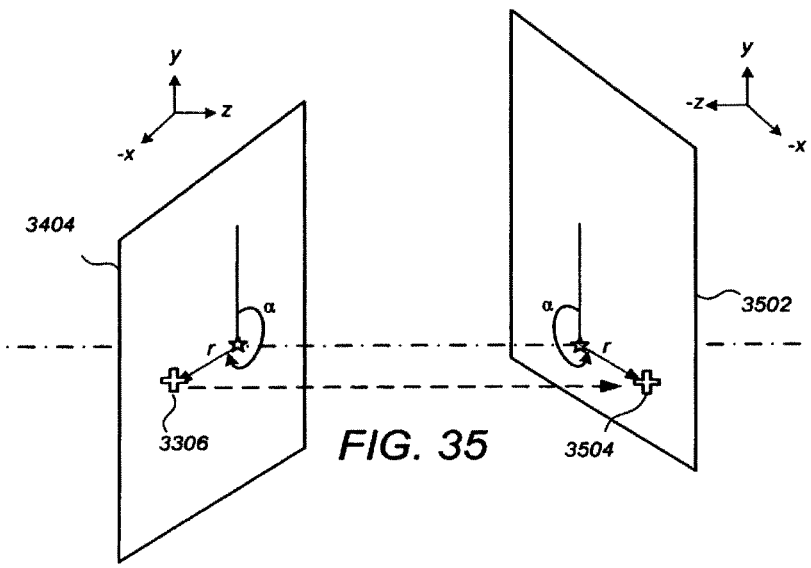
FIGS. 35-36 illustrate transfer of (a) Cartesian offset from the nipple, and (b) depth from the skinline/compressive surface from the first breast ultrasound volume to the second breast ultrasound volume according to a preferred embodiment.
Figure 36:
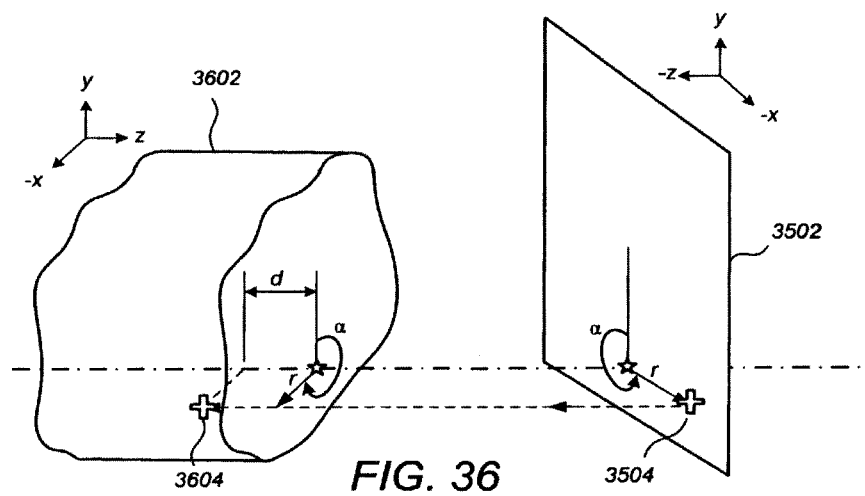

With reference to FIG. 35, that Cartesian offset $(r,\alpha)$ is then transferred to a second coronal reference plane 3502 to identify a transferred offset point 3504 thereon, the second coronal reference plane 3502 passing through the nipple location within the second ultrasonic volume 3602. The transferred offset point 3504 is then backprojected (see FIG. 36) from the second coronal reference plane 3502 into the second ultrasonic volume 3604. The distance "d" in the chestward direction from the nipple is known (see FIG. 34) by virtue of the known thick-slice that was clicked upon, and applied in the backprojection in FIG. 36.

Figure 38:
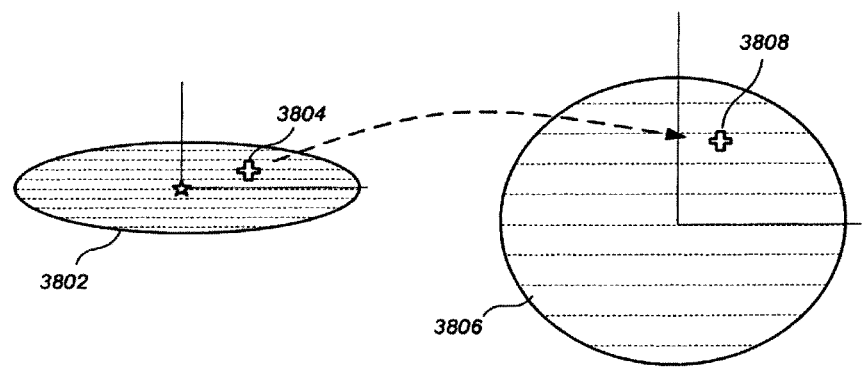
FIG. 38 illustrates a conceptual view of ROI mapping in which accommodations are made for compression of the breast along one or more anti-coronal planes.

In another preferred embodiment, with reference to FIG. 38, accommodations are made for compression of the breast along an anti-coronal plane (i.e., along a plane perpendicular to the coronal plane, which would include CC, MLO, and LAT, for example) during one or both of the volumetric scans. In particular, where the breast was so compressed during the first scan or the second scan (but not both), the transferred point 3804 on the second coronal reference plane 3802 is modified according to an elastic mapping (3802→3806) between a coronal projection 3802 of the anti-coronally-compressed breast onto a coronal projection 3806 of the non-anti-coronally-compressed breast. The "clock position" of the transferred point changes due to an expansion of the breast along the vertical direction in FIG. 38 to a different clock position 3808. The elastic mapping is determined at least in part according to a measured compression force and a distance between compression plates during breast compression along the anti-coronal plane. In one preferred embodiment, the breast can be modeled as a three-dimensional object having known compressibility, and so the compressed outline (as projected onto the coronal plane) can be re-expanded outward where the compression force and the plate distance are known.

If the breast was so compressed for both volumetric scans, the breast being compressed along a first anti-coronal plane during the first volumetric scan thereof and compressed along a second anti-coronal plane during the second volumetric scan thereof, the transferred point on the second coronal reference plane is modified according to an elastic mapping between a coronal projection of the breast as compressed along the first anti-coronal plane and a coronal projection of the breast as compressed along the second anti-coronal plane.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, there can be many different ways of displaying the first ultrasound volume (and, when selected, the source ROI thereon) and the second ultrasound volume (including the destination ROI thereon) without departing from the scope of the preferred embodiments. For example, two side-by-side display monitors can be provided that are each similar to FIG. 18, supra, the first monitor showing the breast as scanned in Year N, and the second monitor showing the breast as scanned from Year N+1. The user can select a particular location of interest in the Year N breast volume on the first monitor, and then invoke a "map" command or similar input. Responsive thereto, the second display would automatically navigate to the appropriate thick-slice and planar images that intersect that selected location in the Year N+1 breast volume. Alternatively, instead of showing Year N and Year N+1 volumes simultaneously on two different monitors, a single monitor can be used to alternate between displaying Year N and Year N+1. Thus, while Year N is being displayed, the user would select a location of interest in the Year N breast volume and then invoke the "map" command or similar input. Responsive thereto, the display would automatically replace the Year N volume with the Year N+1 volume, with the corresponding location in the Year N+1 volume being automatically navigated to and highlighted. When viewing for temporal comparison, this alternative method provides a sort of "time travel" on the user display, because the user is staying in the same location but is being thrust forward or backward in time. When viewing for alternative views taken on the same date (e.g., navigating between a lateral frontal scan and a medial frontal scan of a breast taken during the same session), this alternative method provides a sort of "hyperspace" on the user display, because the user is staying at the same general point in time but is being instantly transported to different views of the ROI. In one illustration, when a suspicious location is occluded (e.g., by shadowing) in the lateral frontal scan, the user can use the above-described methods to instantly view the medial frontal scan at that suspicious location for a clearer view. Therefore, reference to the details of the preferred embodiments are not intended to limit their scope, which is limited only by the scope of the claims set forth below.

Figure 39:
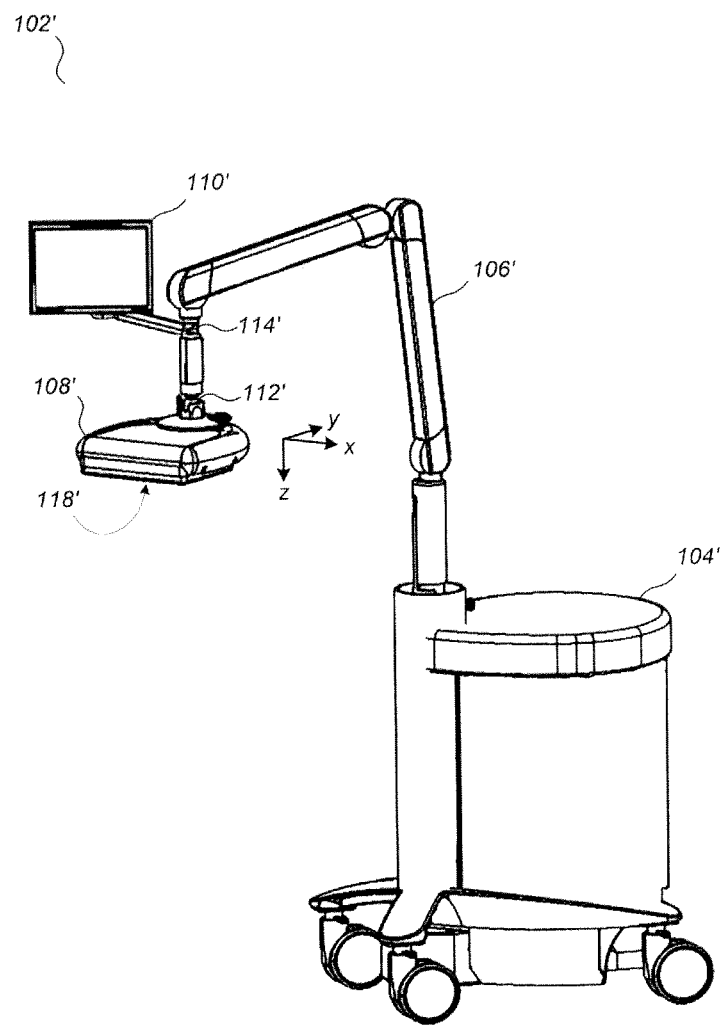
FIG. 39 illustrates a perspective view of a scanning apparatus according to a preferred embodiment.

FIG. 39 illustrates a perspective view of a full-field breast ultrasound (FFBU) scanning apparatus 102' according to a preferred embodiment, comprising a frame 104' that may contain an ultrasound processor, a movable support arm 106', a compression/scanning assembly 108' connected to the support arm 106' via a ball-and-socket connector 112', and a monitor 110' connected to the support arm 106' at a joint 114'. Preferably, the support arm 106' is configured and adapted such that the compression/scanning assembly 108' is either (i) neutrally buoyant in space, or (ii) has a light net downward weight (e.g., 2-3 pounds) for breast compression, while allowing for easy user manipulation. According to a preferred embodiment, the compression/scanning assembly 108' comprises an at least partially conformable membrane 118' in a substantially taut state, the membrane 118' having a bottom surface contacting the breast while a transducer is swept across a top surface thereof to scan the breast. Optionally, the support arm 106' may comprise potentiometers (not shown) to allow position and orientation sensing for the compression/scanning assembly 108', or other types of position and orientation sensing (e.g., gyroscopic, magnetic, optical) can be used. By way of example and not by way of limitation, a miniBIRD® 3D position sensor from Ascension Technologies can be used to determine the position and orientation of the compression/scanning assembly 108' on a per-frame basis.

Within frame 104' may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

The compression/scanning assembly 108' is preferably a substantially self-contained, pod-like module that can be grasped by the hands of a user and manipulated to compress the breast in a generally chestward direction. By generally chestward, it is meant that membrane 118' of the compression/scanning assembly 108' urges the breast surface toward the chest wall of the patient while the membrane is an angle of 45 degrees or less from a coronal plane. It has been found that generally speaking, the breasts of supine or reclining women can have many different tendencies depending on the anatomy of the woman. For example, for first fully supine woman the breast may droop upward toward the shoulder, while for a second fully supine woman the breast may droop downward toward the abdomen or inward toward the sternum. For these breasts it may be desirable to tilt the scanning surface somewhat relative to the coronal plane, obtaining a scan of the breast while pushing the breast at least partially sideways toward the theoretical center of the breast and while also pushing it inward toward the chest wall.

Notably, the scope of the preferred embodiments is not limited to the above-referenced angles relative to the coronal plane. In other preferred embodiments any of a variety of different angles and orientations may be used, depending on the circumstances. Thus, in another example, there may be an older, large-breasted woman with highly pendulous breast tissue. In that case, it may be desirable to have the woman stand upright, and the compression/scanning assembly 108' might be positioned underneath the breast, serving as a sort of platform or table for the breast to rest on. In this case, the membrane 118' would be almost at a 90 degree angle relative to the coronal plane. Depending on the results, the platform could be tilted a little more in the chestward direction to better image the chest wall, e.g., at a 60-75 degree angle relative to the coronal plane. In distinction, for smaller-breasted women, a direct head-on angle of zero degrees relative to the coronal plane will be more appropriate in most cases. The ability to perform scans at this variety of angles is facilitated by providing the end of the support arm 106' with all three translational degrees of freedom (e.g., x, y, and z), and providing the compression/scanning assembly 108' with all three rotational degrees of freedom (e.g., pitch, roll, and yaw) relative to the end of the support arm 106' via the ball-and-socket connector 112'. The monitor 110' is conveniently and movably positioned near the end of the support arm 106' for easy viewing by the user in any of a variety of positions.

Figure 40:
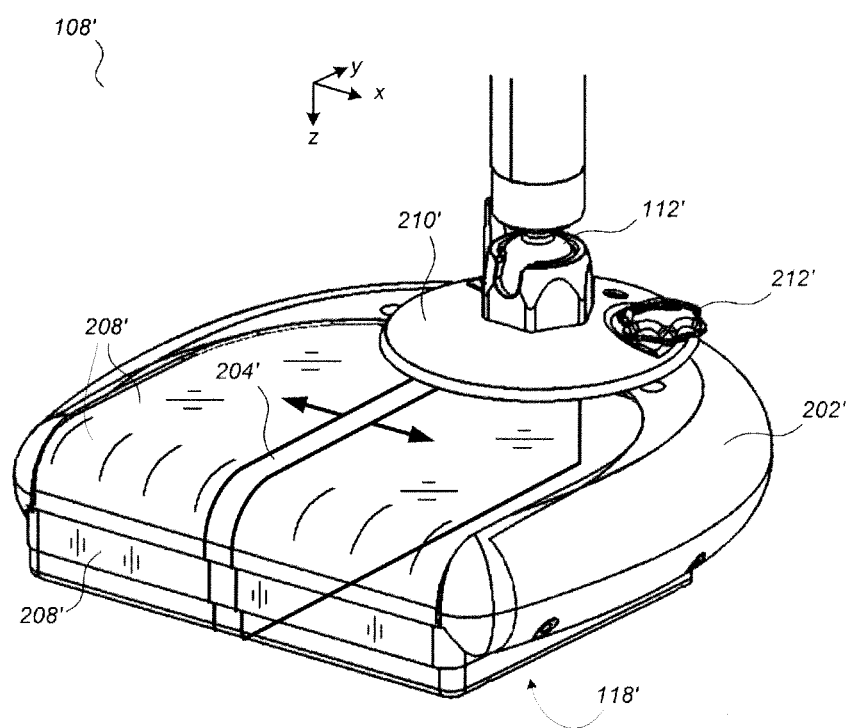
FIG. 40 illustrates a perspective view of a compression/scanning assembly of the scanning apparatus of FIG. 39.

FIG. 40 illustrates a perspective view of the compression/scanning assembly 108', which comprises a housing 202' and a linear array transducer 204'. In one preferred embodiment, the transducer 204' comprises 768 piezoelectric transducer elements. Transducer types other than linear array transducers, such as 1.25D, 1.5D or 2D transducers are also within the scope of the preferred embodiments. The housing 202' forms an opening on its underside, across which is positioned the membrane 118'. In one embodiment, the acoustic coupling at the interface between the transducer 204' and the membrane 118' is facilitated by dynamic or static wetting with water or other low viscosity coupling agent as described, for example, in the commonly assigned WO 2004/030523A2, supra. In another preferred embodiment, a silicone oil can be used to facilitate the acoustic coupling. In one preferred embodiment, the membrane 118' comprises a polyester film sheet. Examples can include 2 mil-thick Mylar® or Melinex®, although a variety of other suitable materials are within the scope of the preferred embodiments.

According to a preferred embodiment, in addition to the membrane 118' comprising an optically transparent material, the housing 202' also comprises an optically transparent portion 208' in areas that would otherwise impede a view of the compressed breast surface. The optically transparent portion 208' can comprise a substantially transparent acrylic or polycarbonate plastic, while the outer non-transparent portions of the housing 202' can comprise any of a variety of thermoform plastics. The transparency of the housing 202' in these areas can make positioning and monitoring of the scanning process much easier, and accordingly improve the quality of the acquired scans. Because normal usage can result in scratches or other degradation of the membrane 118' over time, the membrane 118' is preferably designed to be field-replaceable, such as by using pop-on and pop-off style framing in conjunction with the housing 202', or by using screw-type fasteners or a quick-release lever.

Along a plate 210' is a potentiometer knob 212' that is manually rotated by the user to align a marker thereon with a head-to-toe direction of the patient, thereby providing information to the ultrasound system to orient the scan data. In other preferred embodiments, known anatomical structures visible in the ultrasound images can be used to automatically orient the scans. By way of example, the patient's the rib cage can be segmented from the resulting ultrasound data in order to facilitate automatic orientation of the images.

It is to be appreciated that the scope of the preferred embodiments is not limited to linear array probes performing linear-sweep scans across the surface of the membrane 118'. In other preferred embodiments, any of a variety of scanning motions (e.g., multiple linear sweeps, rotations, targeted scans of predetermined or dynamically determined sub-volumes of the breast, combinations of the above, etc) can be used. In still other preferred embodiments, the scanning surfaces are curved rather than flat, or partially curved along part(s) of the transducer array.

Figure 41:
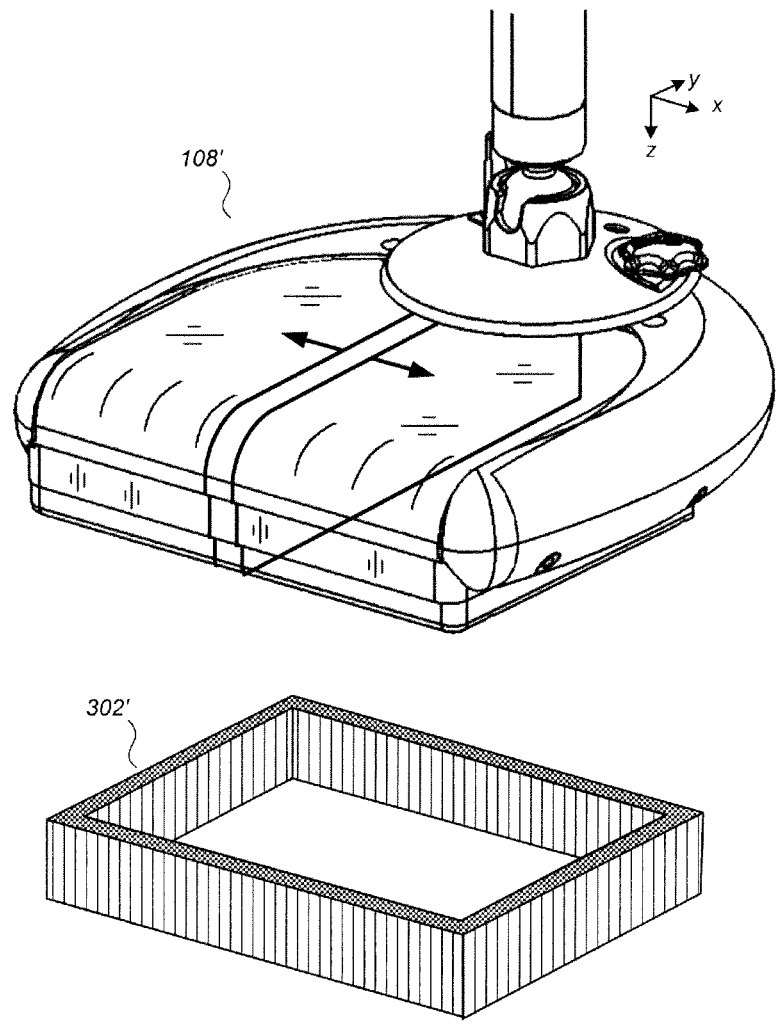
FIG. 41 illustrates a perspective view of the compression/scanning assembly of FIG. 40 and a lateral support element according to a preferred embodiment.

FIG. 41 illustrates a perspective view of the compression/scanning assembly 108' with an attachable lateral support element 302' according to a preferred embodiment. The lateral support element 302' provides for gentle lateral confinement of the breast during the scans. In one preferred embodiment, the lateral support element 302' comprises an at least partially pliable material such as a rubberized sponge material. The lateral support element 302' is particularly useful for larger, pendulous breasts that might otherwise migrate over toward the side, or upward toward the shoulder, of a supine patient. In other preferred embodiments, the lateral support element 302' may instead be provided as a stand-alone element not connected to the compression/scanning assembly 108'. In these preferred embodiments, the lateral support element 302' is laterally positioned around the breast before the compression/scanning assembly 108' is lowered thereon. Any of a variety of pre-formed or user-conformable materials capable of laterally confining the breast are within the scope of the preferred embodiments.

Figure 42:
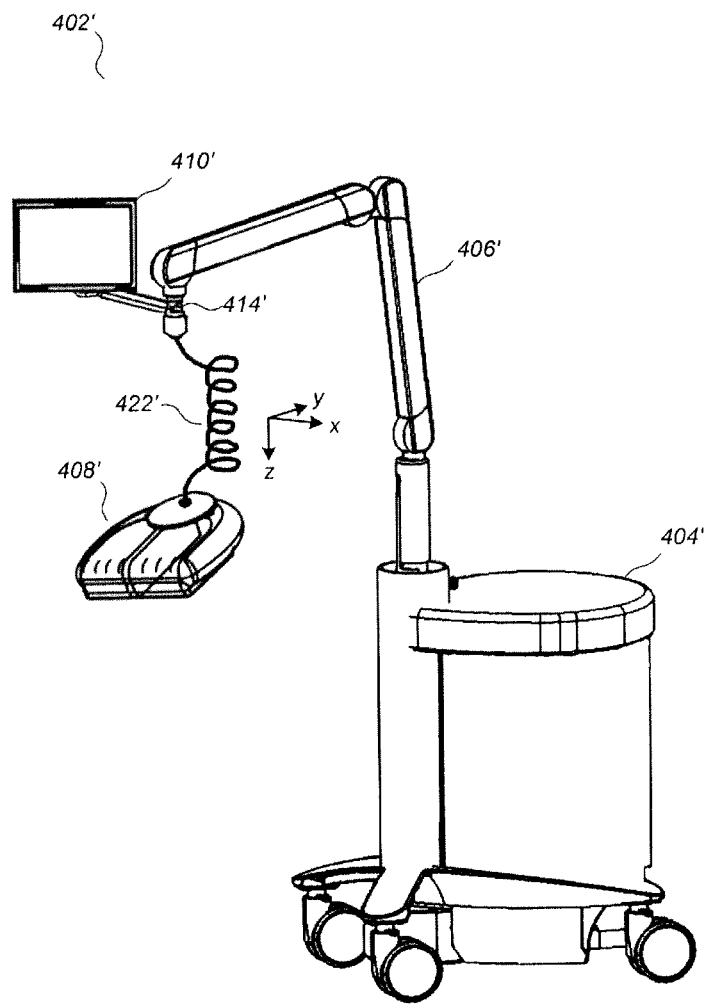
FIG. 42 illustrates a perspective view of a scanning apparatus according to a preferred embodiment.

FIG. 42 illustrates a perspective view of a scanning apparatus 402' according to a preferred embodiment, comprising a frame 404', a support arm 406', a compression/scanning assembly 408', and a monitor 410' connected to the support arm 406' at a joint 414'. The compression/scanning assembly 408' is mechanically separated from the support arm 406', being fully supported and manipulated by the user's hands. However, the compression/scanning assembly 408' is electrically coupled to an ultrasound processor through a cable extending from the support arm 406', the cable also providing backup support by suspending the compression/scanning assembly 408' above the floor in case it is accidentally dropped or otherwise released by the user. Position sensing is optionally provided using gyroscopic means, optical means, magnetic means, etc. (not shown).

In other preferred embodiments, the compression/scanning assembly 408' can completely stand alone, with no physical cables or mechanical connection to the remainder of the overall apparatus. In these embodiments, wireless digital communications or other electromagnetic radiation-based communications can be used to transfer the acquired scans to an ultrasound processor. In still other embodiments, battery power can be used such that not even a power cord is required, making the compression/scanning assembly truly portable.

Figure 43:
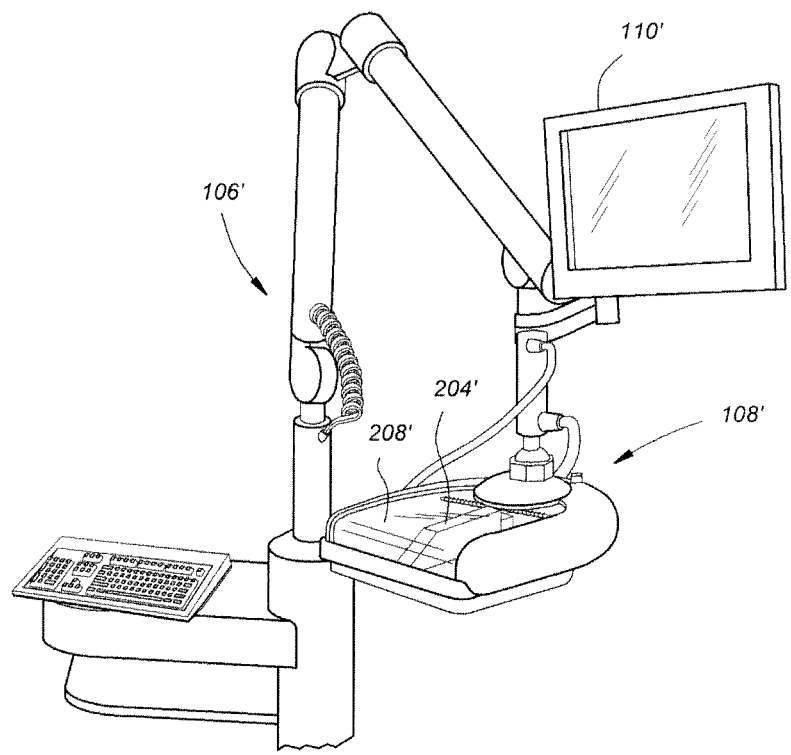
FIG. 43 shows a scanning apparatus according to a preferred embodiment.
Figure 44:
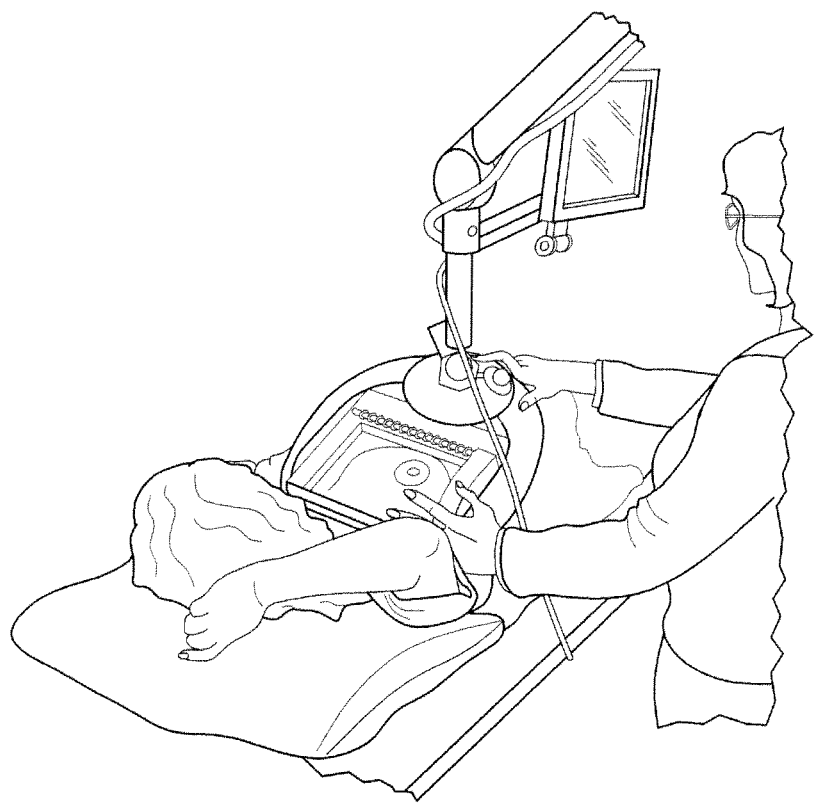
FIGS. 44-48 illustrate the scanning apparatus of FIG. 43 under control of a user while scanning the breasts of a patient according to a preferred embodiment.
Figure 45:
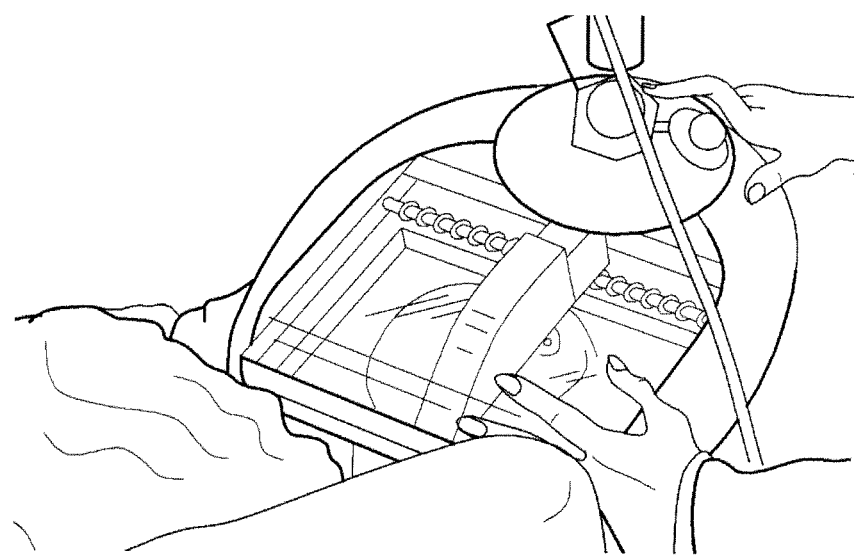
Figure 46:
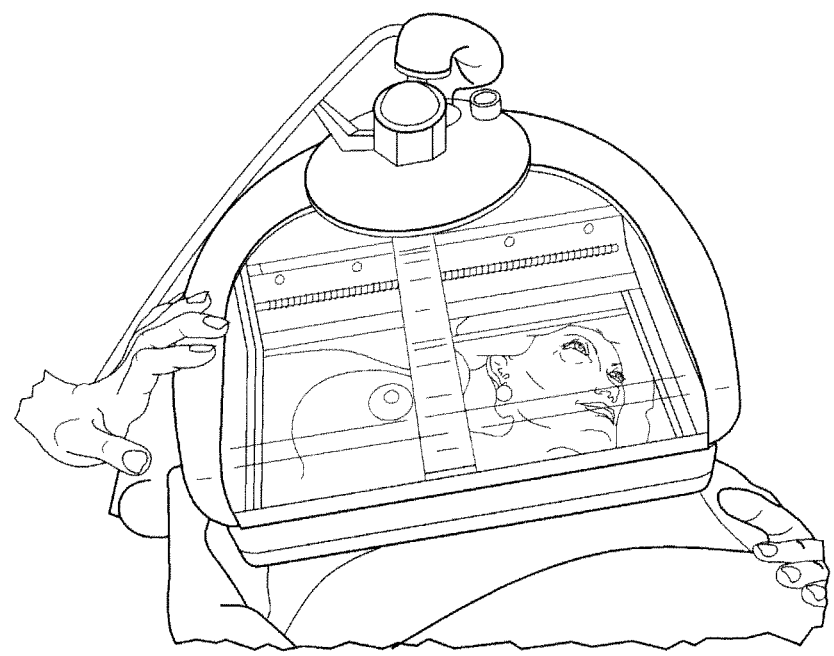
Figure 47:
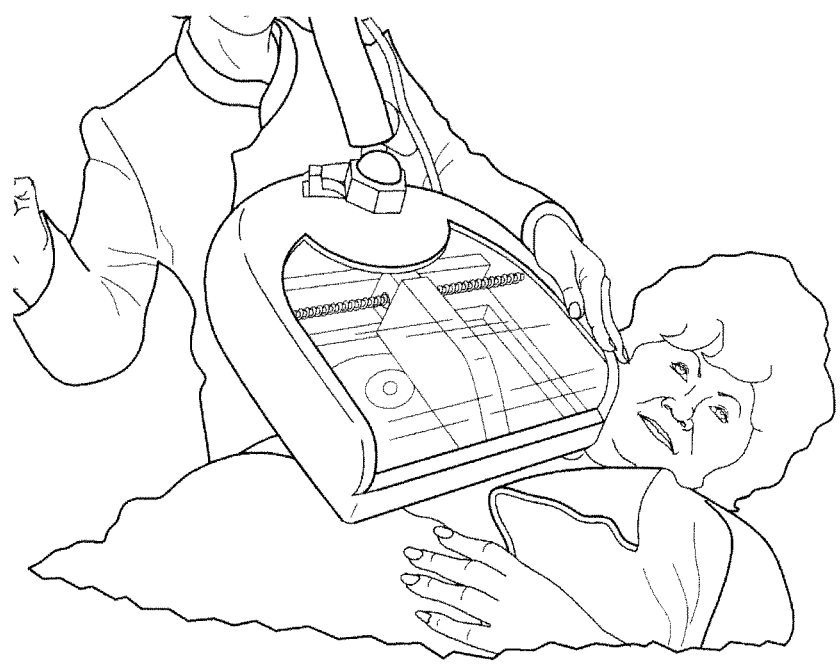
Figure 48:

FIG. 43 illustrates a perspective view of a scanning apparatus similar to that of FIG. 39. FIGS. 44-48 illustrate the scanning apparatus of FIG. 43 under control of a user while scanning the breasts of a patient, illustrating just some of the many different scanning angles and orientations that are facilitated.

In addition to being easy to manipulate, the scanning apparatus further promotes patient comfort and reliable scanning because the patient can comfortably breathe during the procedure without confounding the scanning results, because the compression/scanning assembly rises up and down (or in and out) with the patient's chest. Further position and orientation sensors can optionally be placed on the patient's chest to detect relative motion between the compression/scanning assembly and the patient, where desired. Measurement of respiratory movement can thereby be achieved, and used to during formation of ultrasound volumes from the planar scans by compensating for respiratory movement.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, while described supra in terms of having a membranous compression/scanning surface, in other preferred embodiments the compression/scanning surface can be a thin, rigid material such as polycarbonate plastic, or other materials that are described in U.S. Pat. No. 6,574,499, which is incorporated by reference herein. Therefore, reference to the details of the preferred embodiments are not intended to limit their scope, which is limited only by the scope of the claims set forth below.

What is claimed is: 1. An apparatus for full-field breast ultrasound (FFBU) scanning of a breast of a supine patient, comprising a compression/scanning assembly having an ultrasound transducer and an at least partially conformable membrane in a substantially taut state, the membrane having a first surface for contacting the breast and a second surface opposite the first surface, the transducer being swept across the second surface in contact therewith to scan the breast, wherein the compression/scanning assembly is configured and adapted to be handheld for user positioning thereof against the breast for generally chestward compression of the breast during said scan. 2. The apparatus of claim 1, said compression/scanning assembly comprising a housing within which said transducer is disposed, the housing including an aperture across which the conformable membrane is positioned, wherein said membrane and said housing are optically transparent at locations that allow the user to view the breast surface through the compression/scanning assembly during said positioning and scanning. 3. The apparatus of claim 1, further comprising a frame and a movable support arm coupled to the frame, said compression/scanning assembly being coupled to an end of the support arm, wherein said support arm three translational degrees of freedom relative to the frame, and wherein the compression/scanning assembly has three rotational degrees of freedom relative to the end of the movable support arm. 4. The apparatus of claim 3, said support arm supporting the compression/scanning assembly to be either (i) neutrally buoyant in space, or (ii) to have a light net downward weight (e.g., 2-3 pounds) for breast compression, while allowing for easy user manipulation thereof. 5. The apparatus of claim 1, further comprising a position and orientation sensing system for providing compression/scanning assembly position and orientation information corresponding to said scan. 6. The apparatus of claim 1, further comprising a lateral support element extending from said membrane toward the breast for gentle lateral confinement of the breast during said scans, the lateral support element comprising an at least partially pliable material.

What is claimed is:

1. A system for ultrasound examination of an upwardly facing breast of a supine patient, comprising:
    a support and a compression/scanning module supported thereby and configured to move under hand control of an operator from a non-scanning position above the supine patient and out of contact with the supine patient's breast to a scanning position upon the supine patient and in contact with the breast, the compression/scanning module comprising:
    (i) a housing member supported by the support and shaped for said hand control of the compression/scanning module by the operator, said housing member having a lower opening;
    (ii) an ultrasound transducer movably disposed within said housing member;
    (iii) an ultrasonically transparent compressive membrane secured across said lower opening in said housing member, said membrane and said housing member forming a general enclosure within which said ultrasound transducer is movably maintained, said compressive membrane being positioned to contact the breast and compress the breast in a chestward direction when the compression/scanning module is in said scanning position; and
    (iv) an actuator disposed within said housing member and coupled to the ultrasound transducer and configured, when the compression/scanning module is in said scanning position, to translate the ultrasound transducer across the compressive membrane, said ultrasound transducer thereby scanning the chestwardly compressed breast through said membrane to acquire image data representative of a three-dimensional data volume of a sonographic property of the chestwardly compressed breast;
    wherein said housing member and said membrane are each optically transparent at locations thereon sufficient for the operator to visually observe a skin surface of the chestwardly compressed breast, including a nipple location thereon, through the housing member and through the membrane when the compression/scanning module is in said scanning position;
    a processor configured to receive and process the image data representative of the three-dimensional data volume to generate therefrom (a) a plurality of two-dimensional coronal ultrasound images, each coronal ultrasound image representing said sonographic property of the chestwardly compressed breast along one of a slice and slab subvolume thereof substantially parallel to a coronal plane of the patient, and (b) a plurality of two-dimensional axial ultrasound images, each axial ultrasound image representing said sonographic property of the chestwardly compressed breast along one of a slice and slab subvolume thereof substantially parallel to an axial plane of the patient; and
    a computerized display configured to receive and selectively display said coronal ultrasound images and said axial ultrasound images;
    wherein said processor is further configured to receive information indicative of said nipple location as visually observed and indicated by the operator with said compression/scanning module in said scanning position and to process said information indicative of the nipple location in conjunction with said image data representative of the three-dimensional data volume to determine a nipple location corresponding to each of said coronal ultrasound images; and wherein said computerized display is further configured to display a nipple marker with each said coronal ultrasound image at said determined nipple location thereon.

2. The system of claim 1, wherein each of said plurality of coronal ultrasound images is a coronal thick-slice image representing said sonographic property of the chestwardly compressed breast along a slab subvolume thereof substantially parallel to the coronal plane of the patient and having a thickness in the range of about 2 mm-20 mm.

3. The system of claim 1, wherein each of said plurality of coronal ultrasound images is a coronal thin-slice image representing said sonographic property of the chestwardly compressed breast along a thin slice thereof substantially parallel to the coronal plane of the patient.

4. The system of claim 1, wherein said processor is further configured to receive at least one viewer input indicative of whether each said displayed coronal ultrasound image is desired to be (i) a coronal thick-slice image representing said sonographic property of the chestwardly compressed breast along a slab subvolume thereof substantially parallel to the coronal plane of the patient and having a thickness in the range of about 2 mm-20 mm, or (ii) a coronal thin-slice image representing said sonographic property of the chestwardly compressed breast along a thin slice thereof substantially parallel to the coronal plane of the patient and thinner than said thick-slice subvolume, and wherein said processor is further configured to generate each said coronal ultrasound image from said image data according to said at least one viewer input.

5. The system of claim 1, the computerized display being further configured to display concurrently with said coronal ultrasound images:
 a body marker icon representative of a frontal view of the breast; and
 a graphical outline upon said body marker icon indicative of a frontal area of the breast scanned by the ultrasound transducer in said automated translation across the compressive membrane.

6. The system of claim 5, further comprising a user interface including a pointing device for manipulation by a user, wherein said computerized display is further configured to display:
 a cursor positioned upon one of said coronal ultrasound images according to user manipulation of the pointing device; and
 a frontal breast icon including a central location thereof, said frontal breast icon including a cursor position indicator variably positioned thereon relative to said central location in a manner that reflects a relative position between said cursor and said nipple marker on said coronal thick-slice image, the cursor position indicator moving relative to said center location on said frontal breast icon as the cursor moves relative to said nipple marker on said coronal ultrasound image responsive to the user manipulation of the pointing device.

7. The system of claim 1, wherein said computerized display is further configured to display a rotatable, three-dimensionally-appearing version of the three-dimensional data volume.

8. The system of claim 1, said housing member comprising a rigid upper surface opposite said lower opening, wherein said rigid upper surface consists of an optically transparent material to thereby allow the operator to visually observe the skin surface of the chestwardly compressed breast through both the rigid upper surface and the membrane when the compression/scanning module is in said scanning position.

9. A method for ultrasound examination of an upwardly facing breast of a supine patient, comprising:
 providing a compression/scanning module comprising a housing member, an ultrasound transducer movably disposed within said housing member, an ultrasonically transparent compressive membrane secured across a lower opening defined in said housing member, said membrane and said housing member forming a general enclosure within which said ultrasound transducer is movably maintained, and an automated translation assembly disposed within said housing member and coupled to the ultrasound transducer;
 selectively manipulating, by an operator, the compression/scanning module from a non-scanning position above the supine patient and out of contact with the breast to a scanning position in which the compressive membrane of the compression/scanning module compresses the breast in a chestward direction, wherein after the compression/scanning assembly is in said scanning position the automated translation assembly translates the ultrasound transducer across the compressive membrane to thereby scan the chestwardly compressed breast therethrough to acquire image data representative of a three-dimensional data volume of a sonographic property of the chestwardly compressed breast;
 wherein said housing member and said membrane are each optically transparent at locations thereon sufficient for the operator to visually observe a skin surface of the chestwardly compressed breast, including a nipple location thereon, through the housing member and through the membrane when the compression/scanning module is in said scanning position;
 computer processing the image data representative of the three-dimensional data volume to generate therefrom (a) a plurality of two-dimensional coronal ultrasound images, each coronal ultrasound image representing said sonographic property of the chestwardly compressed breast along one of a slice and slab subvolume thereof substantially parallel to a coronal plane of the patient, and (b) a plurality of two-dimensional axial ultrasound images, each axial ultrasound image representing said sonographic property of the chestwardly compressed breast along one of a slice and slab subvolume thereof substantially parallel to an axial plane of the patient;
 wherein said computer processing further comprises processing information indicative of said nipple location as visually observed and indicated by the operator in conjunction with said image data to determine a nipple location for each of said coronal ultrasound images; and
 displaying said coronal ultrasound images and said axial ultrasound images on a computerized display, said coronal ultrasound images each including a nipple marker thereon at said determined nipple location.

10. The method of claim 9, wherein each of said plurality of coronal ultrasound images is a coronal thick-slice image representing said sonographic property of the chestwardly compressed breast along a slab subvolume thereof substantially parallel to the coronal plane of the patient and having a thickness in the range of about 2 mm-20 mm.

11. The method of claim 9, wherein each of said plurality of coronal ultrasound images is a coronal thin-slice image representing said sonographic property of the chestwardly compressed breast along a thin slice thereof substantially parallel to the coronal plane of the patient.

12. The method of claim 9, further comprising receiving, at a user interface associated with said computerized display, at least one input from a viewer of the computerized display indicative of whether each said displayed coronal ultrasound image is desired to be (i) a coronal thick-slice image representing said sonographic property of the chestwardly compressed breast along a slab subvolume thereof substantially parallel to the coronal plane of the patient and having a thickness in the range of about 2 mm-20 mm, or (ii) a coronal thin-slice image representing said sonographic property of the chestwardly compressed breast along a thin slice thereof substantially parallel to the coronal plane of the patient and thinner than said thick-slice subvolume, wherein said computer processing comprises generate each said coronal ultrasound image according to said at least one viewer input.

13. The method of claim 9, wherein said displaying said coronal ultrasound images further comprises displaying:
 a body marker icon representative of a frontal view of the breast; and
 a graphical outline upon said body marker icon representing a frontal area of the breast scanned by the ultrasound transducer in said automated translation across the compressive membrane.

14. The method of claim 13, further comprising receiving, at a user interface associated with said computerized display, inputs corresponding to manipulations of a pointing device by a viewer, wherein said displaying said coronal ultrasound images further comprises displaying:
 a cursor positioned upon one of said coronal ultrasound images according to the user manipulation of the pointing device; and
 a frontal breast icon including a central location, said frontal breast icon including a cursor position indicator variably positioned thereon relative to said central location in a manner that reflects a relative position between said cursor and said nipple marker on said coronal thick-slice image, the cursor position indicator moving relative to said center location on said frontal breast icon as the cursor moves relative to said nipple marker on said coronal ultrasound image responsive to the viewer manipulation of the pointing device.

15. The method of claim 9, wherein said computerized display further displays a rotatable, three-dimensionally-appearing version of the three-dimensional data volume.

16. The method of claim 9, wherein said housing member comprises a rigid upper surface opposite said lower opening, wherein said rigid upper surface consists of an optically transparent material to thereby allow the operator to visually observe the skin surface of the chestwardly compressed breast through both the rigid upper surface and the membrane when the compression/scanning module is in said scanning position.

* * * * *